US010209330B2

(12) United States Patent
Bottomley et al.

(10) Patent No.: US 10,209,330 B2
(45) Date of Patent: Feb. 19, 2019

(54) SYSTEM AND METHOD OF PERFORMING MAGNETIC RESONANCE SPECTROSCOPIC IMAGING

(75) Inventors: Paul A. Bottomley, Baltimore, MD (US); Refaat Gabr, Baltimore, MD (US); Yi Zhang, Baltimore, MD (US); Robert G. Weiss, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 1507 days.

(21) Appl. No.: 14/006,069

(22) PCT Filed: Mar. 22, 2012

(86) PCT No.: PCT/US2012/030176
§ 371 (c)(1),
(2), (4) Date: Sep. 18, 2013

(87) PCT Pub. No.: WO2012/129433
PCT Pub. Date: Sep. 27, 2012

(65) Prior Publication Data
US 2014/0015529 A1    Jan. 16, 2014

Related U.S. Application Data

(60) Provisional application No. 61/466,188, filed on Mar. 22, 2011.

(51) Int. Cl.
*G01R 33/46* (2006.01)
*G01R 33/485* (2006.01)
*G01R 33/483* (2006.01)

(52) U.S. Cl.
CPC ........... *G01R 33/46* (2013.01); *G01R 33/483* (2013.01); *G01R 33/485* (2013.01)

(58) Field of Classification Search
CPC ..... G01R 33/483; G01R 33/485; G01R 33/46
See application file for complete search history.

(56) References Cited

U.S. PATENT DOCUMENTS

| 4,776,863 A | 10/1988 | van den Berg et al. |
| 5,128,629 A | 7/1992 | Trinh |

(Continued)

FOREIGN PATENT DOCUMENTS

| JP | H08-191816 A | 7/1996 |
| JP | 2001-095773 A | 4/2001 |
| KR | 10-2008-0027135 A | 3/2008 |

OTHER PUBLICATIONS

Akoka et al., "Radiofrequency map of an NMR coil by imaging," Magn Reson Imaging 11, 437-441 (1993).

(Continued)

*Primary Examiner* — Rishi Patel
(74) *Attorney, Agent, or Firm* — Venable LLP; Henry J. Daley

(57) ABSTRACT

A method of performing spatially localized magnetic resonance spectroscopy includes receiving a magnetic resonance image of an object; identifying a plurality C of compartments that generate magnetic resonance spectroscopy signals in the object including at least one compartment of interest; segmenting in at least one spatial dimension the magnetic resonance image of the object into the C compartments; acquiring magnetic resonance spectroscopy signals from the compartments by applying a plurality of M' phase encodings applied in the at least one spatial dimension, wherein M'≥C; calculating a spatially localized magnetic resonance chemical shift spectrum from the at least one compartment of interest; and rendering a spatially localized magnetic resonance spectrum that is substantially equal to a spatial average of magnetic resonance chemical shift spectra (Continued)

from the at least one compartment of interest. A magnetic resonance spectroscopy and imaging system is configured to perform the above method.

17 Claims, 14 Drawing Sheets

(56) References Cited

U.S. PATENT DOCUMENTS

| | | | |
|---|---|---|---|
| 5,214,372 | A | 5/1993 | Vaisanen et al. |
| 5,903,149 | A | 5/1999 | Gonen et al. |
| 5,982,165 | A | 11/1999 | Bowyer et al. |
| 6,310,646 | B1 | 10/2001 | Shi et al. |
| 6,426,623 | B1 | 7/2002 | Bernstein |
| 6,521,874 | B2 | 2/2003 | Thompson et al. |
| 7,098,646 | B2 | 8/2006 | Rose |
| 7,652,464 | B2 | 1/2010 | Lang et al. |
| 7,822,565 | B2 | 10/2010 | Brouk et al. |
| 2003/0151453 | A1 | 8/2003 | Laletin |
| 2004/0100325 | A1 | 5/2004 | van Amerom |
| 2005/0130595 | A1 | 6/2005 | Shurvinton et al. |
| 2005/0227625 | A1 | 10/2005 | Diener |
| 2007/0242715 | A1 | 10/2007 | Gustaysson et al. |
| 2007/0249928 | A1 | 10/2007 | Blezek et al. |
| 2007/0252597 | A1* | 11/2007 | Posse .................. G01R 33/485 324/312 |
| 2008/0177163 | A1 | 7/2008 | Wang et al. |
| 2008/0280583 | A1 | 11/2008 | Chattopadhyay et al. |
| 2009/0251926 | A1 | 10/2009 | Choi et al. |
| 2011/0066025 | A1 | 3/2011 | Bahn |
| 2011/0148411 | A1 | 6/2011 | Bottomley et al. |
| 2011/0152673 | A1 | 6/2011 | Doerr et al. |
| 2013/0134976 | A1 | 5/2013 | Sugiura |
| 2013/0144140 | A1 | 6/2013 | Frederick et al. |
| 2014/0015529 | A1 | 1/2014 | Bottomley et al. |
| 2014/0015547 | A1 | 1/2014 | Bottomley et al. |

OTHER PUBLICATIONS

Baker et al., "Evaluation of specific absorption rate as a dosimeter of MRI-related implant heating," J Magn Reson Imaging 20, 315-320 (2004).
Basser et al., MR diffusion tensor spectroscopy and imaging. Biophys J 1994;66(1):259.
Biswal et al., Functional connectivity in the motor cortex of resting human brain using echo-planar mri. Magn Reson Med 1995;34(4):537-541.
Borthakur et al,, Sodium and T1p MRI for molecular and diagnostic imaging of articular cartilage. NMR Biomed 2006;19(7):781-821.
Bottomley et al., "RF magnetic field penetration, phase-shift and power dissipation in biological tissue: implications for NMR Imaging," Physics in Medicine and Biology 23, 630-643 (1978).
Bottomley et al., "Homogeneous tissue model estimates of RF power deposition in human NMR studies—local elevations predicted in surface coil decoupling," Ann. N.Y. Acad. Sci. 649, 144-159 (1992).
Bottomley et al., "Power deposition in whole-body NMR imaging," Med Phys 8, 510-512 (1981).
Bottomley et al., A review of normal tissue hydrogen NMR relaxation times and relaxation mechanisms from 1-100 MHz: dependence on tissue type, NMR frequency, temperature, species, excision, and age. Med Phys 1984;11:425.
Bottomley et al., Fourpangle saturation transfer (FAST) method for measuring creatine kinase reaction rates in vivo. Magn Reson Med 2002;47(5):850-863.
Bottomley, "Turning up the heat on MRI," Journal of the American College of Radiology 5, 853-855 (2008).
Bottomley et al., "Designing passive MRI-safe implantable conducting leads with electrodes," Med Phys 37, 3828-3843 (2010).
Bottomley et al., "Estimating radiofrequency power deposition in body NMR imaging," Magn Reson Med 2, 336-349 (1985).
Brix et al., "Sampling and evaluation of specific absorption rates during patient examinations performed on 1.5-Tesla MR systems," Magn Reson Imaging 19, 769-779 (2001).
Chavhan et al., Principles, Techniques, and Applications of T2*-based MR Imaging and Its Special Applications 1. Radiographics 2009;29(5)1433-1449.
Collins et al., "Calculation of radiofrequency electromagnetic fields and their effects in MRI of human subjects," Magn Reson Med 65, 1470-1482 (2011).
Collins et al., "SAR and Bi field distributions in a heterogeneous human head model within a birdcage coil. Specific energy absorption rate," Magn Reson Med 40, 847-856 (1998).
Collins et al., "Temperature and SAR calculations for a human head within volume and surface coils at 64 and 300 MHz," J Magn Reson Imaging 19, 650-656 (2004).
Detre et al., Perfusion imaging. Magn Reson Med 1992;23(1):37-45.
Edelstein et al., "Electronic method for eliminating prescanning RF transmitter amplitude adjustment", Society of Magnetic Resonance in Medicine Sixth Annual Meeting, p. 372. New York, NY, USA, (1987).
Edelstein et al., "The intrinsic signal-to-noise ratio in NMR imaging," Magn Reson Med 3, 604-618 (1986).
Ehsesv et al., "MRI thermometry: Fast mapping of RF-induced heating along conductive wires," Magn Reson Med 60, 457-461 (2008).
El-Sharkawy et al., "The performance of interventional loopless MRI antennae at higher magnetic field strengths," Med Phys 35, 1995-2006 (2008).
Ei-Sharkawy et al., "A Multi-Channel, High Dynamic Range, Real Time RF Power Deposition Monitor", Proc Int Soc Magn Reson Med p. 496. Montreal, Canada, (2011).
Ei-Sharkawy et al., "Accurate Measurement of RF Power Deposition During 3T MRI", 18th Annual Meeting, Int Soc Magn Reson Med p. 3853. Stockholm, Sweden, (2010).
Forsén et al., Study of moderately rapid chemical exchange reactions by means of nuclear magnetic double resonance. The Journal of Chemical Physics 1963;39(11):2892-2901.
Guidance for Industry and FDA: "Staff Criteria for Significant Risk Investigations of Magnetic Resonance Diagnostic Devices, " United States Food and Drug Administration (FDA), 2003.
Hoge et al., A tour of accelerated parallel MR imaging from a linear systems perspective. Concepts Magn Reson Part A 2005;27(1)17-37.
Homann, et al., "Toward individualized SAR models and in vivo validation," Magn Reson Med 66, 1767-1776 (2011).
Ibrahim et al., "Analysis of B 1 field profiles and SAR values for multi-strut transverse electromagnetic RF coils in high field MRI applications," Physics in Medicine and Biology 46, 2545-2555 (2001).
Ibrahim et al., "Dielectric resonances and B(1) field inhomogeneity in UHFMRI: computational analysis and experimental findings," Magn Reson Imaging 19, 219-226 (2001).
International Search Report and Written Opinion of PCT/2012/030173.
Kim et al., Water saturation shift referencing (WASSR) for chemical exchange saturation transfer (CEST) experiments. Magn Reson Med 2009;61(6):1441-1450.
Kumar et al., "Noise figure limits for circular loop MR coils," Magn Reson Med 61, 1201-1209 (2009).
Liu et al., "Calculations of B-1 distribution, specific energy absorption rate, and intrinsic signal-to-noise ratio for a body-size birdcage coil loaded with different human subjects at 64 and 128 MHz," Appl. Magn. Reson, 29, 5-18 (2005).
Loan CFV. The ubiquitous Kronecker product. J Comput Appl Math 2000;123(1):85-100.
Mattei et al., "MRI induced heating of pacemaker leads: effect of temperature probe positioning and pacemaker placement on lead tip heating and local SAR," Conf Proc IEEE Eng Med Biol Soc 1, 1889-1892 (2006).

(56) References Cited

OTHER PUBLICATIONS

Muranaka et al., "Dependence of RF heating on SAR and implant position in a 1.5T MR system," Magn Reson Med Sci 6, 199-209 (2007).

Nguyen et al., "Numerical evaluation of heating of the human head due to magnetic resonance imaging," IEEE Trans Biomed Eng 51, 1301-1309 (2004).

Nitz, et al., "Specific absorption rate as a poor indicator of magnetic resonance-related implant heating," Invest Radiol 40, 713-776 (2005).

Oh et al., "Experimental and numerical assessment of MRI-induced temperature change and SAR distributions in phantoms and in vivo," Magn Reson Med 63, 218-223 (2010).

Posse et al., MR spectroscopic imaging: principles and recent advances. J Magn Reson Imaging 2013;37(6):1301-1325.

Pruessmann et al., Advances in sensitivity encoding with arbitrary k-space trajectories. Magn Reson Med 2001;46(4):638-651.

Pruessmann et al., SENSE: sensitivity encoding for fast MRI. Magn Reson Med 1999;42(5):952-962.

Schar et al., "Simultaneous B(o)– and B(1)+-map acquisition for fast localized shim, frequency, and RF power determination in the heart at 3 T," Magn Reson Med 63, 419-426 (2010).

Schär et al., Triple repetition time saturation transfer (TRiST) 31P spectroscopy for measuring human creatine kinase reaction kinetics. Magn Reson Med 2010;63(6):1493-1501.

Shellock, "Comments on MR heating tests of critical implants," J Magn Reson Imaging 26, 1182-1185 (2007).

Simunic, "Calculation of energy absorption in a human body model in a homogeneous pulsed high-frequency field," Bioelectrochem. Bioenerg. 47, 221-230 (1998).

Stralka et al., "A prototype RF dosimeter for independent measurement of the average specific absorption rate (SAR) during MRI," J Magn Reson Imaging 26, 1296-1302 (2007).

Wang et al., "Theoretical and experimental investigation of the relationship among SAR, tissues and radio frequencies in MRI," Physica Medica 21, 61-64 (2005).

Wang et al., "SAR and temperature: simulations and comparison to regulatory limits for MRI," J Magn Reson Imaging 26, 437-441 (2007).

Ward et al., A new class of contrast agents for MRI based on proton chemical exchange dependent saturation transfer (CEST). J Magn Reson 2000;143(1):79-87.

Weber et al., "A ultra high field multi-element transceive volume array for small animal MRI," Conf Proc IEEE Eng Med Biol Soc 2008, 2039-2042 (2008).

Weiss et al., ATP flux through creatine kinase in the normal, stressed, and failing human heart. Proc Natl Acad Sci U S A 2005;102(3):808-813.

Wolff et al., Magnetization transfer contrast (MTC) and tissue water proton relaxation in vivo. Magn Reson Med 1989;10(1):135-144.

Zaremba, "FDA Guidelines for Magnetic Resonance Equipment Safety", The American Association of Physicists in Medicine Annual Meeting, p. 8356. Palais des Congres de Montreal, (2002).

Zhang et al., Highly-accelerated quantitative 2D and 3D localized spectroscopy with linear algebraic modeling (SLAM) and sensitivity encoding. J Magn Reson 2013;237:125-138.

Zhou et al., Practical data acquisition method for human brain tumor amide proton transfer (APT) imaging. Magn Reson Med 2008;60(4):842-849.

Zhou et al., Three-dimensional amide proton transfer MR imaging of gliomas: Initial experience and comparison with gadolinium enhancement. J Magn Reson Imaging 2013;38(5):1119-1128.

Ehses et al., "MRI Thermometry: Fast Mapping of RF-Inducted Heating Along Conductive Wires," Mag. Res. Med. 60:457-461 (2008).

Office Action in U.S. Appl. No. 14/005,804, dated Feb. 2, 2017.

Office Action in U.S. Appl. No. 14/005,804, dated Sep. 22, 2016.

Notice of Allowance in U.S. Appl. No. 14/005,804, dated Jun. 26, 2017.

Zhang et al., "Magnetic resonance Spectroscopy with Linear Algebraic Modeling (SLAM) for higher speed and sensitivity," Journal of Magnetic Resonance, Mar. 28, 2012, vol. 218, pp. 66-76.

An et al., Spectral localization by imaging using multielement receiver coils, Magnetic Resonance in Medicine, (2011).

Bashir et al., Natural linewidth chemical shift imaging (NLqCSI), Magnetic Resonance in Medicine, 56 (2006) 7-18.

Beer et al., Neubauer, Absolute concentrations of high-energy phosphate metabolites in normal, hypertrophied, and failing human myocardium measured noninvasively with 31P-SLOOP magnetic resonance spectroscopy, J Am Coll Cardiol, 40 (2002) 1267-1274.

Bottomley et al., Problems and expediencies in human 31P spectroscopy. The definition of localized volumes, dealing with saturation and the technique-dependence of quantification, NMR in Biomedicine, 2 (1989) 284-289.

Bottomley et al., Strategies and Protocols for Clinical 31P Research in the Heart and Brain, Phil. Trans. R. Soc. Lond. A, 333 (1990) 531-544.

Bottomley, NMR Spectroscopy of the Human Heart, in: R.K. Harris, R.E. Wasylishen (Eds.) Encyclopedia of Magnetic Resonance, John Wiley: Chichester, 2009.

Bottomley, Spatial localization in NMR spectroscopy in vivo, Annal NY Acad Sci, 508 (1987) 333-348.

Brooker et al., Selective Fourier transform localization, Magnetic Resonance in Medicine, 5 (1987) 417-433.

Brown et al., NMR chemical shift imaging in three dimensions, Proc. Natl Acad Sci USA, 79 (1982) 3523-3526.

Conway et al., Mitral regurgitation: impaired systolic function, eccentric hypertrophy, and increased severity are linked to lower phosphocreatine/ATP ratios in humans, Circulation, 97 (1998) 1716-1723.

Dong et al., Lipid signal extraction by SLIM: Application to 1H MR spectroscopic imaging of human calf muscles, Magnetic Resonance in Medicine, 55 (2006) 1447-1453.

Ei-Sharkawy et al., Quantitative cardiac 31P spectroscopy at 3 Tesla using adiabatic pulses, Magnetic Resonance in Medicine, 61 (2009) 785-795.

Frahm et al., Localized high-resolution proton NMR spectroscopy using stimulated echoes: Initial applications to human brain in vivo, Magnetic Resonance in Medicine, 9 (1989) 79-93.

Gabr et al., Quantifying in vivo MR spectra with circles, Journal of Magnetic Resonance, 179 (2006) 152-163.

Hu et al., SLIM: spectral localization by imaging, Magnetic Resonance in Medicine, 8 (1988) 314-322.

Jacob et al., Liang, Improved model-based magnetic resonance spectroscopic imaging, Medical Imaging, IEEE Transactions on, 26 (2007) 13051318.

Khalidov et al., BSLIM: Spectral Localization by Imaging With Explicit BO Field Inhomogeneity Compensation, Medical Imaging, IEEE Transactions on, 26 (2007) 990-1000.

Kmiecik et al., Lactate quantitation in a gerbil brain stroke model by GSLIM of multiple-quantum-filtered signals, J Magn Reson Imaging, 9 (1999) 539-543.

Liang et al., Constrained reconstruction methods in MR imaging, Rev Magn Reson Med, 4 (1992) 67-185.

Liang et al., A generalized series approach to MR spectrocpic imaging, IEEE Transactions Medical Imaging, 10 (1991) 132-137.

Loffler et al., Localized spectroscopy from anatomically matched compartments: improved sensitivity and localization for cardiac 31P MRS in humans, Journal of Magnetic Resonance, 134 (1998) 287-299.

Meininger et al., Concentrations of human cardiac phosphorus metabolites determined by SLOOP 31P NMR spectroscopy, Magnetic Resonance in Medicine, 41 (1999) 657-663.

Ordidge et al., Image-selected in vivo spectroscopy (ISIS). A new technique for spatially selective NMR spectroscopy, Journal of Magnetic Resonance (1969), 66 (1986) 283-294.

Panych et al., PSFqchoice: A novel MRI method for shaping pointO spread functions in phase 1:encoding dimensions, Magnetic Resonance in Medicine, 54 (2005) 159-168.

Smith et al., Altered Creatine Kinase Adenosine Triphosphate Kinetics in Failing Hypertrophied Human Myocardium, Circulation, 114 (2006) 1151-1158.

(56) References Cited

OTHER PUBLICATIONS von Kienlin et al., Advances in human cardiac 31P-MR spectroscopy: SLOOP and clinical applications, J Magn Reson Imaging, 13 (2001) 521-527.

von Kienlin et al., Spectral localization with optimal pointspread function, Journal of Magnetic Resonance, 94 (1991) 268-287.

Weiss et al., ATP flux through creatine kinase in the normal, stressed, and failing human heart, Proc Nati Acad Sci USA, 102 (2005) 808-813.

Weiss et al., Regional Myocardial Metabolism of High-Energy Phosphates during Isometric Exercise in Patients with Coronary Artery Disease, N Engl J Med, 323 (1990) 1593-1600.

Zhang et al., Dramatic speedup in 1D-, 2D- and 3D- MRS scan times with linear algebraic modeling (SLAM), in: Proceedings of the International Society for Magnetic Resonance in Medicine, in press, 2012.

International Search Report and Written Opinion of PCT/US2012/030176.

\* cited by examiner

| Comparison | SLIM | GSLIM | SLOOP | SLAM* | fSLAM* |
|---|---|---|---|---|---|
| Method | CSI phase-encoding and MRI-based compartment selection. | CSI phase-encoding and MRI-based compartment selection. | CSI phase-encoding. The phase-encode gradients may be optimized for minimum bleed when compartments are non-uniform. | CSI phase-encoding but only the C central k-space steps are selected to optimize SNR. | Starting from MRI, central k-space phase-encodes are selected to optimize SNR with errors & contamination minimized |
| Assumption | Every compartment is uniform. | Non-uniform compartments in SLIM can be addressed using non-Fourier basis sets (generalized series). | Uniform compartments but gradients can be adjusted to minimize inter-compartment bleed for non-uniform compartments. | The compartment spectrum is the average of the CSI spectra from each compartment. | The compartment spectrum is the average of the CSI spectra in each compartment, with SNR optimized and minimum error vs CSI. |
| Gradient Optimization | Not optimized | Not optimized | May be optimized for SNR and minimum inter-compartment leakage. | SNR optimized using minimum number of central k-space phase-encodes. | Optimized for SNR, inter-compartment leakage and intra-compartment error. |
| Gradient Step | Stepped as ~n/FOV, n =...-2,-1,0,1,2... (integer). | Stepped as ~n/FOV, n =...-2,-1,0,1,2... (integer). | Stepped as ~p/FOV, p integer or non-integer (if optimized). | Stepped as ~n/FOV, with -C/2 ≤ n ≤ C/2, n integer | Stepped per optimization, maximum gradient limited by compartment size. |
| Reconstruction | Using the CSI signal set, compartment signal is computed from the integral of the signal contributing to each compartment. | Compartment signal is computed from CSI signals same as SLIM, followed by a general series constrained modeling to minimize errors. | Compartmental signal is computed from the CSI signal set as the integral of the signal contributing to each compartment. | Starting from CSI, phase-encode steps are eliminated down to C compartments. | Signals acquired with pro-actively optimized phase-encodes are reconstructed same as SLAM. |
| Errors | Exact for large n. Inter- and intra-compartmental errors arise for small n. | Reduces leakage for finite n by applying general series modeling to the SLIM result. | Inter-compartment leakage suppressed vs SLIM. Error from intra-compartment non-uniformity remains. | Errors increase as number of phase encodes decrease. | Both inter-compartmental bleed and intra-compartmental error are suppressed. |
| In vivo human use | Applied to conventional 1H CSI data of lipid (retro-actively acquired) from human calf. | None. | Applied to conventional 31P CSI data retro-actively acquired from human heart. | Applied both to retro-actively acquired CSI, and pro-actively acquired SLAM human cardiac 31P data. | fSLAM applied pro-actively in human cardiac 31P MRS. |

FIG. 11

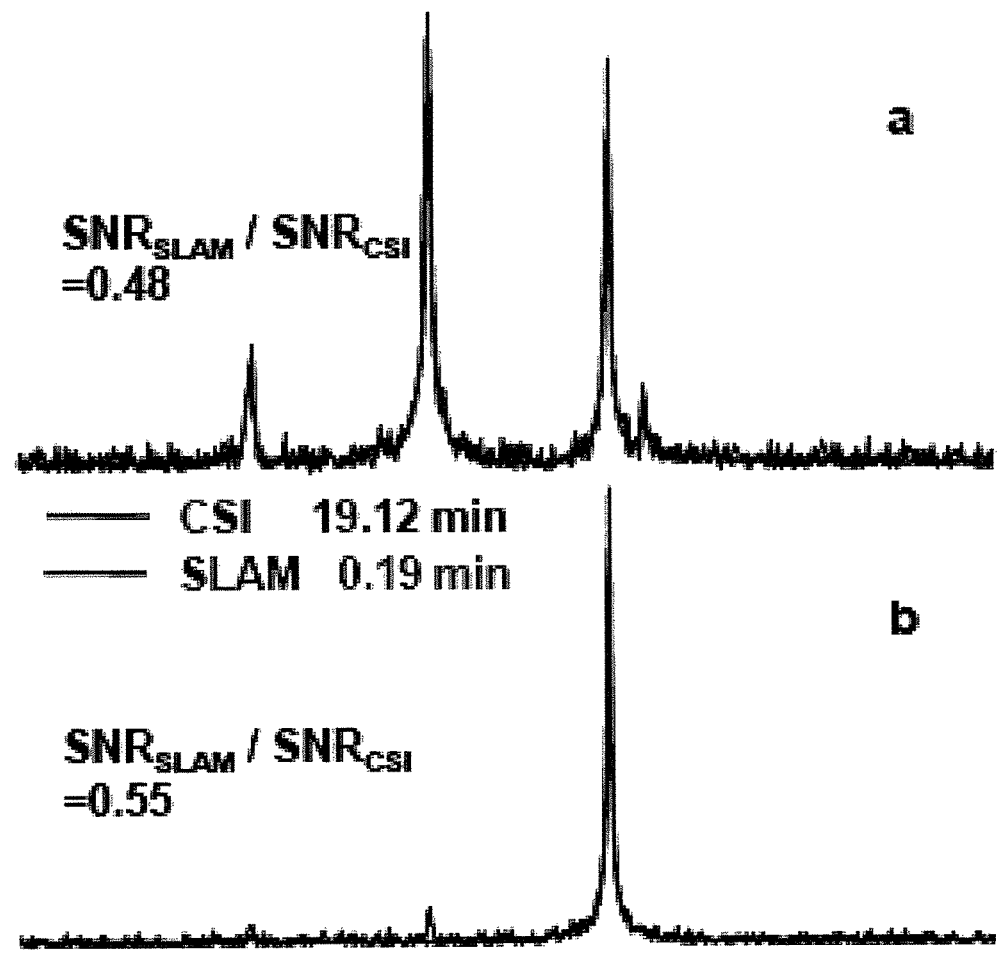
FIGS. 14 A and 14B

SYSTEM AND METHOD OF PERFORMING MAGNETIC RESONANCE SPECTROSCOPIC IMAGING

This invention was made with U.S. Government support of Grant Nos. EB007829 and HL61912 awarded by the National Institutes of Health. The U.S. Government has certain rights in the invention.

This is a national stage application under 35 U.S.C. § 371 of PCT/US2012/030176 filed Mar. 22, 2012, the entire contents of which are incorporated herein by reference and this application claims priority to U.S. Provisional Application No. 61/466,188 filed Mar. 22, 2011, the entire contents of which are hereby incorporated by reference.

BACKGROUND

1. Field of Invention

The field of the currently claimed embodiments of this invention relates to systems and methods of spatially localized magnetic resonance spectroscopy.

2. Discussion of Related Art

Long scan time is a major problem for multi-voxel magnetic resonance spectroscopy (MRS) and chemical shift imaging (CSI). While model-based MRS reconstruction methods, such as SLIM [Hu X, et al. MRM 1988; 8:314-322], GSLIM [Liang Z P, et al. IEEE TMI 1991; 10:132-137] and SLOOP [von Kienlin M, et al. JMR 1991; 94:268-287] could reduce scan times in theory, their in vivo application remains very limited and focused on suppression of inter-compartment leakage [Dong Z, et al. MRM 2006; 55; 1447-1453; Loffler R, et al. JMR 1998; 134:287-299] using entire CSI datasets. A significant speed advantage from these methods, has, to the best of our knowledge, not been realized in vivo or in humans, and it is unknown whether such speed-ups could be achieved with at least the same accuracy as CSI in practice. There thus remains a need for improved systems and methods of magnetic resonance spectroscopic imaging.

SUMMARY

A method of performing spatially localized magnetic resonance spectroscopy according to an embodiment of the current invention includes receiving a magnetic resonance image of an object; identifying a plurality C of compartments that generate magnetic resonance spectroscopy signals in the object including at least one compartment of interest; segmenting in at least one spatial dimension the magnetic resonance image of the object into the C compartments; acquiring magnetic resonance spectroscopy signals from the compartments by applying a plurality of M' phase encodings applied in the at least one spatial dimension, wherein M'≥C; calculating a spatially localized magnetic resonance chemical shift spectrum from the at least one compartment of interest; and rendering a spatially localized magnetic resonance spectrum that is substantially equal to a spatial average of magnetic resonance chemical shift spectra from the at least one compartment of interest.

A magnetic resonance localized spectroscopy and imaging system according to an embodiment of the current invention includes a magnetic resonance imaging scanner and a data processing system configured to communicate with the magnetic resonance imaging scanner to receive magnetic resonance spectroscopy signals of an object. The data processing system is configured to receive a magnetic resonance image of the object; display the magnetic resonance image to permit identification of a plurality C of compartments that generate magnetic resonance spectroscopy signals in the object and that includes at least one compartment of interest; segment in at least one spatial dimension the magnetic resonance image of the object into the C compartments; receive magnetic resonance spectroscopy signals from the object corresponding to the magnetic resonance image by applying a plurality M' of phase encodings in at least one spatial dimension, wherein M'≥C; calculate a spatially localized magnetic resonance chemical shift spectrum from the at least one compartment of interest; and provide a spatially localized magnetic resonance spectrum substantially equal to the spatial average of the magnetic resonance chemical shift spectra from the at least one compartment of interest.

BRIEF DESCRIPTION OF THE DRAWINGS

Further objectives and advantages will become apparent from a consideration of the description, drawings, and examples.

(FIG. 8B) $^{31}$P spectra acquired from a normal human heart from the same 4-voxel volume, using 1D CSI in 8.4 min, and SLAM spectra reconstructed with a subset of 4 central k-space phase-encodes and a 4-compartment model. (FIG. 8C) Spectra acquired with just two phase-encodes and a 2-compartment model (chest and heart). The effective SLAM acquisition times were $\frac{1}{4}^{th}$ and $\frac{1}{8}^{th}$ of CSI.

FIG. 11 is a table showing a comparison of some embodiments of the current invention with conventional approaches.

FIGS. 14A and 14B show an example of a 3D phantom $^{31}$P MRS (same volume, SLAM 100 times faster).

DETAILED DESCRIPTION

Figure 1:
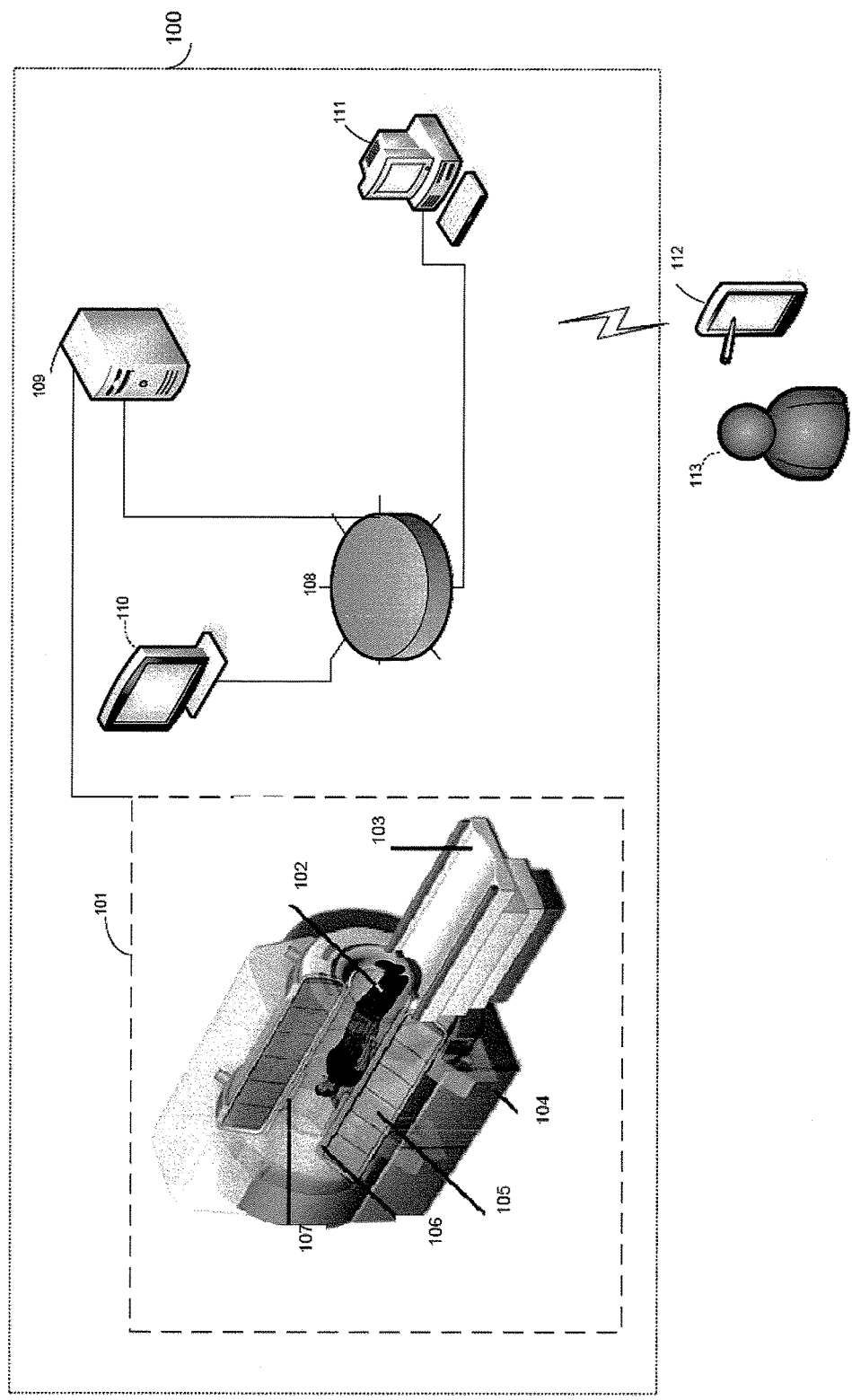
FIG. 1 is a schematic illustration of magnetic resonance localized spectroscopy and imaging system according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Speed and signal-to-noise ratio (SNR) are central requirements for localized magnetic resonance spectroscopy (MRS) of low-concentration metabolites. Matching voxels to anatomical compartments a priori yields better SNR than the spectra created by summing signals from constituent chemical-shift-imaging (CSI) voxels post-acquisition. Here, a new method of localized spectroscopy using linear algebraic modeling (SLAM) according to an embodiment of the current invention is provided that can realize such additional SNR gain. Unlike prior methods, SLAM generates spectra from C signal-generating anatomic compartments utilizing a CSI sequence wherein only the C central k-space phase-encoding gradient steps with highest SNR are retained. After MRI-based compartment segmentation, the spectra are reconstructed by solving a sub-set of linear simultaneous equations from the standard CSI algorithm. Some examples of SLAM are provided with one-dimensional CSI surface coil phosphorus MRS in phantoms, the human leg and the heart on a 3T clinical scanner. Its SNR performance, accuracy, sensitivity to registration errors and inhomogeneity, are evaluated. Compared to one-dimensional CSI, SLAM yielded quantitatively the same results 4-times faster in 24 cardiac patients and healthy subjects, and 45% higher cardiac SNR when applied pro-actively to 6 additional subjects. SLAM can be further extended according to an embodiment of the current invention with fractional phase-encoding gradients that optimize SNR and/or minimize both inter- and intra-compartmental contamination. In cardiac $^{31}$P MRS of 6 healthy subjects, fractional-SLAM (fSLAM) produced results indistinguishable from CSI while preserving SNR gains of 30-40% in the same scan-time. Both SLAM and fSLAM are simple to implement and reduce minimum scan times for CSI, which otherwise limits scan-time reductions achievable with higher SNR and field strengths. However, the broad concepts of the current invention are not limited to these particular embodiments and examples.

Some concepts of the current invention can be described by the following examples. Scan-time and signal-to-noise ratio (SNR) are major problems for in vivo spatially localized magnetic resonance spectroscopy (MRS) of low-concentration metabolites. Because SNR is proportional to voxel size, matching the voxel to the desired anatomical compartment a priori yields the best SNR for a fixed scan time [1]. Consider for example a first chemical shift imaging (CSI) experiment [2] encoding a voxel V with an SNR of 20 per acquisition. Averaging n=4 acquisitions yields an SNR of 40 since SNR adds as √n. Now consider a second experiment performed at four times the resolution with V/4-sized voxels. The SNR/voxel is now 5 per acquisition because noise is independent of voxel size [1]. Phase-encoding is equivalent to averaging, so after 4 gradient steps to encode the same volume, the SNR per voxel is 10. Adding the 4 signals to make a V-sized voxel now yields an SNR of 20, again because of the √n rule. This compares to 40 from the first experiment. Thus, the SNR for the same scan-time and voxel size is doubled in the first experiment, just by pre-selecting the correct voxel size to start with [1].

The same principle applies in general wherever the CSI voxel size is smaller than the object of interest. The SNR gain factor for a fixed scan-time obtained by correctly encoding a compartment at the outset, as compared to adding signals from individual CSI voxels to form the equivalent-sized compartment post-acquisition, is:

$$g = \sqrt{\frac{\text{compartment size}}{\text{CSI voxel size}}}, \qquad (1)$$

notwithstanding the effects of nonuniform sensitivity and concentration distributions, or differences in the integrated spatial response function (SRF). This differential g-fold SNR gain vs. CSI can be seen as arising from the time lost by CSI in acquiring the low SNR, high gradient-strength, high k-space signals.

Prior phase-encoding gradient based MRS localization methods such as SLIM[3], GSLIM[4] and SLOOP[5], could realize the g-fold SNR gain if the desired compartments were prescribed from scout MRI prior to acquisition, and if an appropriately SNR-optimized gradient set were then applied. In SLIM, the compartment's signal is modeled as the integral of phase-encoded signal contributions in each compartment, assumed homogeneous. The approach is prone to inter- and intra-compartmental errors when metabolite distributions are non-uniform between [6] and within each compartment, and as the number of phase-encoding gradient steps are reduced. GSLIM[4] and SLOOP[5] were introduced to minimize the inter-compartmental errors. GSLIM does this by applying non-Fourier, generalized series modeling to the SLIM result[4, 6]. SLOOP minimizes the inter-compartmental error by optimizing the SRF for the desired compartment, ideally by specifically tailoring the phase-encoding gradient set for the acquisition[5]. Several other proposed improvements add constraints to deal with inhomogeneity in the main ($B_0$) field[7-9], registration errors[9], and multi-element receivers[10].

Even though all of these techniques can generate spectra from multiple compartments from the same data set, they are seldom used pro-actively for human MRS. Thus, SLIM was applied retroactively to $^1$H CSI data sets acquired from the human calf[3, 11] and brain[9], and both GSLIM and SLIM were used in $^1$H MRS CSI acquisitions from a gerbil brain[12]. Although SLOOP$^1$H MRS was initially performed with proactively optimized gradients on an excised rabbit kidney[5], all subsequent applications to human heart applied SLOOP retroactively to $^{31}$P MRS data acquired with regular CSI gradients[13-16]. Because all of these human applications employed conventional CSI gradient sets and uniform k-space sampling, a g-fold SNR advantage versus CSI, beyond that obtained by simply summing the signals from the constituent CSI voxels or accounting for differences in the integrated SRF, was not realized or reported. The lack of pro-active implementation and absence of a demonstrated SNR advantage have likely contributed to the failure of these methods to supplant routine CSI. In any case, the prescribing of compartments and tailoring of gradient encoding steps to match the desired compartment and achieve the full SNR gain predicted by Eq. (1) has, to the best of our knowledge, never been realized in vivo or in humans.

According to an embodiment of the current invention, we apply a sharply-reduced SNR-optimized gradient set to perform localized spectroscopy with linear algebraic modeling (SLAM) to acquire and reconstruct average spectra from C signal-generating anatomical compartments that are identified by scout MRI, routinely acquired for spatially-localized MRS. Spectral reconstruction for this new SLAM method differs from SLIM, GSLIM and SLOOP in that it solves, by matrix analysis, a set of linear simultaneous equations essentially equal to C (provided that all signal-generating tissues are included) by eliminating un-needed phase-encoding steps from the standard CSI algorithm. The SLAM pulse sequence differs in that the number of phase-encoding steps is essentially C, and they are always selected from the center of the integer-stepped k-space of CSI where SNR is highest. Other than determining the number, C, the need for image-guided gradient optimization, prescription and implementation at the scanner-side prior to acquisition, is thus avoided. Using SLAM, g-fold SNR gains of 30-200% SNR are demonstrated in 3T phosphorus ($^{31}$P) studies of the human leg and heart in vivo, compared to conventional[17-22] one-dimensional (1D) CSI spectra from the same net volume and scan-time. Moreover, we show that application of SLAM to raw $^{31}$P 1D CSI data acquired from heart patients and scout MRI-based segmentation yields, after discarding 75% of the data, essentially the same quantitative measures of adenosine triphosphate (ATP) and phosphocreatine (PCr), four-times faster.

According to another embodiment of the current invention, we extend the SLAM approach to allow for fractional gradient increments instead of conventional, integer-stepped, CSI gradients. In this "fSLAM" method, the phase-encoding gradients are pro-actively optimized at the scanner-side to maximize SNR and/or minimize both the inter-compartmental leakage as well as the intra-compartmental errors produced by nonuniform signal distributions. Intra-compartmental errors have not been addressed in prior methods [3-5]. An example of fSLAM according to an embodiment of the current invention is demonstrated in pro-active human cardiac $^{31}$P studies.

FIG. 1 is a schematic illustration of a magnetic resonance spectroscopy and imaging (MRSI) system 100 according to an embodiment of the current invention. The MRSI system 100 includes a magnetic resonance scanner 101, a data storage unit 108, and a data processing unit 109. Magnetic resonance scanner 101 has a main magnet 105 providing a substantially uniform main magnetic field $B_0$ for a subject (or object) 102 under observation on scanner bed 103, a gradient system 106 providing a perturbation of the main magnetic field $B_0$ to encode spatial information of the constituent molecules of subject 102 under observation, and a radio-frequency (RF) coil system 107 to transmit electromagnetic waves and to receive magnetic resonance signals from subject 102.

Data storage unit 108 may be, for example, a hard disk drive, a network area storage (NAS) device, a redundant array of independent disks (RAID), a flash drive, an optical disk, a magnetic tape, a magneto-optical disk, etc. However, the data storage unit 108 is not limited to these particular examples. It can include other existing or future developed data storage devices without departing from the scope of the current invention.

The data processing system 109 is in communication with magnetic resonance scanner 101 to receive magnetic resonance signals for forming magnetic resonance images of subject 102. Data processing system 109 may be partially or totally incorporated within a structure housing magnetic resonance scanner 101. Data processing system 109 may be partially or totally incorporated in a workstation that is structurally separate from and in communication with magnetic resonance scanner 101. Data processing system 109 may be incorporated in a workstation that is structurally separate from and in communication with magnetic resonance scanner 101. An operator 113 may interact with the MRSI system 100 with input/output device 112.

The data processing system 109 is configured to receive a magnetic resonance image of the object; display the magnetic resonance image to permit identification of a plurality C of compartments that generate magnetic resonance spectroscopy signals in the object and that includes at least one compartment of interest; segment in at least one spatial dimension the magnetic resonance image of the object into the C compartments; receive magnetic resonance spectroscopy signals from the object corresponding to the magnetic resonance image by applying a plurality M' of phase encodings in at least one spatial dimension, where M'≥C; calculate a spatially localized magnetic resonance chemical shift spectrum from at least one compartment of interest; and provide a spatially localized magnetic resonance spectrum substantially equal to the spatial average of magnetic resonance chemical shift spectra from the at least one compartment of interest.

The calculating of the spatially localized magnetic resonance chemical shift spectrum from the at least one compartment of interest can use a linear algebraic method.

The magnetic resonance spectroscopy and imaging scanner can be further configured to permit identification and segmentation of the C compartments prior to receiving the magnetic resonance spectroscopy signals from the object. The magnetic resonance spectroscopy and imaging scanner can be further configured to optimize the M' phase encodings for at least one of the signal-to-noise ratio or the spatial selection in the at least one compartment of interest. In an embodiment, the plurality M' of phase encodings can be provided from a central portion of a k-space corresponding to the at least one spatial dimension of the magnetic resonance image of the object. In an embodiment, the at least one of the plurality M' of phase encodings can be an integer multiple of a smallest non-zero phase encoding. In an embodiment, the at least one of the plurality M' of phase encodings can be a non-integer multiple of a smallest non-zero phase encoding. In an embodiment, the plurality M' of phase encodings can be determined from the magnetic resonance image after segmentation, the data processing system can be further configured to perform at least one of (1) optimization of the signal-to-noise ratio in the at least one compartment of interest which includes the selection of phase encodings from a central portion of the k-space of the magnetic resonance image of the object, or (2) optimization of the spatial selection of the at least one compartment of interest by minimization of at least one of the magnetic resonance spectroscopy signal arising from outside of the compartment of interest, or of erroneous signals arising from non-uniform magnetic resonance spectroscopy signal distributions arising within the compartment of interest.

In an embodiment, the plurality M' of phase encodings can be provided by including a metric that optimizes both the signal-to-noise ratio and the spatial selection in the at least one compartment of interest. In an embodiment, the at least one spatial dimension is one of two spatial dimensions or three spatial dimensions, and the plurality M' of phase encodings includes two or three subsets of phase encodings that are applied in the two or the three spatial dimensions, respectively. In an embodiment, the number of phase encodings provided in each of the subset of phase encodings is greater than or equal to the number of compartments generating magnetic resonance spectroscopy signals that are segmented in the corresponding spatial dimensions of the object. In an embodiment, the at least one compartment of interest can be a plurality of compartments of interest.

The following describes some theoretical aspects in more detail. However, the broad concepts of the current invention are not limited to the particular theory.

Theory

Consider the basic equation for 1D CSI:

$$s(k,t) = \iint \rho(x,f) e^{-i2\pi(kx+ft)} df \, dx \quad (2)$$

where k is the spatial frequency, s(k,t) is the acquired time-domain signal and $\rho(x,f)$ is the spectrum to reconstruct. Since localization is in the spatial domain which is independent of the frequency domain, we denote the spectrum at spatial position x after s(k,t) is Fourier transformed (FT), as $\rho(x)$ in the spectral frequency domain. Assuming there are M phase encoding steps, $k_1 \ldots k_M$, Eq. (2) is discretized as:

$$\begin{bmatrix} s(k_1) \\ s(k_2) \\ \vdots \\ s(k_M) \end{bmatrix}_{M \times N} = \begin{bmatrix} e^{-i2\pi k_1 x_1/M} & e^{-i2\pi k_1 x_2/M} & \ldots & e^{-i2\pi k_1 x_M/M} \\ e^{-i2\pi k_2 x_1/M} & e^{-i2\pi k_2 x_2/M} & \ldots & e^{-i2\pi k_2 x_M/M} \\ \vdots & \vdots & \ddots & \vdots \\ e^{-i2\pi k_M x_1/M} & e^{-i2\pi k_M x_2/M} & \ldots & e^{-i2\pi k_M x_M/M} \end{bmatrix}_{M \times M} \times \begin{bmatrix} \rho(x_1) \\ \rho(x_2) \\ \vdots \\ \rho(x_M) \end{bmatrix}_{M \times N}. \quad (3)$$

Each row of the known signal matrix, $S_{M \times N}$, on the left side of the equation is an N-point array, where N is the number of time-domain data points. The first matrix on the right side is the phase-encoding FT operator (PE), and each term of the unknown spectral matrix, $\rho$, is also an N-point array. For simplicity, we write Eq. (3) as: $S_{M \times N} = PE_{M \times M} \times \rho_{M \times N}$.

Localized Spectroscopy Using a Linear Algebraic Model (SLAM)

The goal of the CSI experiment is to reconstruct the M unknown spectra in matrix $\rho$ of Eq. (3), from the M known signals (S) acquired with M different phase-encodes. However, from scout MRI we learn that $\rho$ has just C<M MRS compartments of interest, as well as the spatial position of each compartment. Theoretically, only C measurements with C phase-encoding steps are needed to unambiguously solve $\rho$ and reconstruct the C spectra.

To illustrate, consider a 4-voxel 1D CSI experiment. Denoting the exponential terms by $e_{i,j}$, Eq. (3) becomes:

$$\begin{bmatrix} e_{11} & e_{12} & e_{13} & e_{14} \\ e_{21} & e_{22} & e_{23} & e_{24} \\ e_{31} & e_{32} & e_{33} & e_{34} \\ e_{41} & e_{42} & e_{43} & e_{44} \end{bmatrix} \times \begin{bmatrix} \rho_1 \\ \rho_2 \\ \rho_3 \\ \rho_4 \end{bmatrix} = \begin{bmatrix} s_1 \\ s_2 \\ s_3 \\ s_4 \end{bmatrix}. \quad (4)$$

Now suppose that from prior information, the second and third rows of $\rho$ are the same ($\rho_2 = \rho_3$). Then we need only solve:

$$\begin{bmatrix} e_{11} & e_{12}+e_{13} & e_{14} \\ e_{21} & e_{22}+e_{23} & e_{24} \\ e_{31} & e_{32}+e_{33} & e_{34} \\ e_{41} & e_{42}+e_{43} & e_{44} \end{bmatrix} \times \begin{bmatrix} \rho_1 \\ \rho_2 \\ \rho_4 \end{bmatrix} = \begin{bmatrix} s_1 \\ s_2 \\ s_3 \\ s_4 \end{bmatrix}. \quad (5)$$

Eq. (5) is now over-determined and can be solved with three phase-encoding rows. The minimum number of required phase-encoding steps is reduced from 4 to 3.

The same theory shows that we can reconstruct C spectra from C homogeneous compartments, with only C phase-encoding steps instead of M steps, regardless of k-space truncation. In general, prior information is incorporated via a b-matrix which zeros out identical rows in the p-matrix to retain only one spectrum for each compartment:

$$S_{M \times N} = PE_{M \times M} \times b_{M \times M}^{-1} \times b_{M \times M} \times \rho_{M \times M} \quad (6)$$

where PE is the phase-encoding operator from Eq. (3). For SLAM based on the 1D CSI experiment, the b-matrix is an identity matrix with "−1" elements inserted to zero out identical rows in ρ. For example, for an 8-voxel CSI experiment performed on a two-compartment sample in which the first compartment extends from voxels 1-3 and the second extends from voxels 4-8, $$b = \begin{bmatrix} 1 & 0 & 0 & 0 & 0 & 0 & 0 & 0 \\ -1 & 1 & 0 & 0 & 0 & 0 & 0 & 0 \\ -1 & 0 & 1 & 0 & 0 & 0 & 0 & 0 \\ 0 & 0 & 0 & 1 & 0 & 0 & 0 & 0 \\ 0 & 0 & 0 & -1 & 1 & 0 & 0 & 0 \\ 0 & 0 & 0 & -1 & 0 & 1 & 0 & 0 \\ 0 & 0 & 0 & -1 & 0 & 0 & 1 & 0 \\ 0 & 0 & 0 & -1 & 0 & 0 & 0 & 1 \end{bmatrix}. \quad (7)$$

Here, only the spectra in voxels 1 (compartment 1) and 4 (compartment 2) are kept after dimensional reduction.

If we choose M'≥C pre-defined phase-encoding steps, and eliminate identical rows to reduce the dimension of $b_{M \times M} \times \rho_{M \times N}$ from M to C, Eq. (6) shrinks to, $$S_{M' \times N} = PE_{M' \times C}^{r} \times \rho_{C \times N}^{r} \quad (8)$$

where $\rho_{C \times N}^{r}$ is a submatrix of $b_{M \times M} \times \rho_{M \times N}$ retaining the C non-eliminated rows; $PE_{M' \times C}^{r}$ is a submatrix of $PE_{M' \times M} \times b_{M \times M}^{-1}$ that retains the C columns corresponding to the C non-eliminated eliminated rows; and $S_{M' \times N}$ is a submatrix of $S_{M \times N}$ signals acquired from the sample using a subset of M'<<M phase-encoding steps. Solution of Eq. (8) results in a set of spectra, each of which closely approximates the average spectrum of each 1D CSI compartment.

The SLAM Recipe

In summary, the SLAM embodiment is performed with Steps 1-5 as follows:
1. Acquire an MRI to extract the prior knowledge of the number of compartments (C<<M), and the spatial position of each compartment for SLAM reconstruction.
2. Choose M'≥C phase-encoding steps. Theoretically, these can be chosen arbitrarily, but different choices will lead to different SNR and different condition numbers for the matrix $PE_{M' \times C}^{r}$ which affect computational accuracy [23]. Of the M original CSI phase-encoding steps, selecting the M' steps that are closest to the center of k-space generally yields the best SNR. Because the set of CSI steps are discrete, fixed and finite, choosing only those from central k-space results in a SLAM phase-encoding gradient set that is determined only by the number M' or C. Moreover, because C is typically the same for a given study protocol (eg, C=4 for cardiac studies with adipose, chest muscle, heart, ventricular blood compartments), the same SLAM gradient set can be used for all the studies, eliminating the need for scanner-side gradient optimization or image-based gradient prescription.
3. Apply the chosen M' encoding gradients and acquire the M' signals.
4. Determine the b matrix from the spatial position of each compartment identified by MRI.
5. Reduce the dimensions from M to C and compute the C spectra in the $\rho^{r}$ matrix using:

$$\rho_{C \times N}^{r} = PE_{C \times N}^{+} \times S_{M' \times N} \quad (9)$$

where $PE_{C \times M'}^{+}$ is the inverse (M'=C) or pseudo-inverse (M'≥C) of $PE_{M' \times C}^{r}$.

Figure 2:
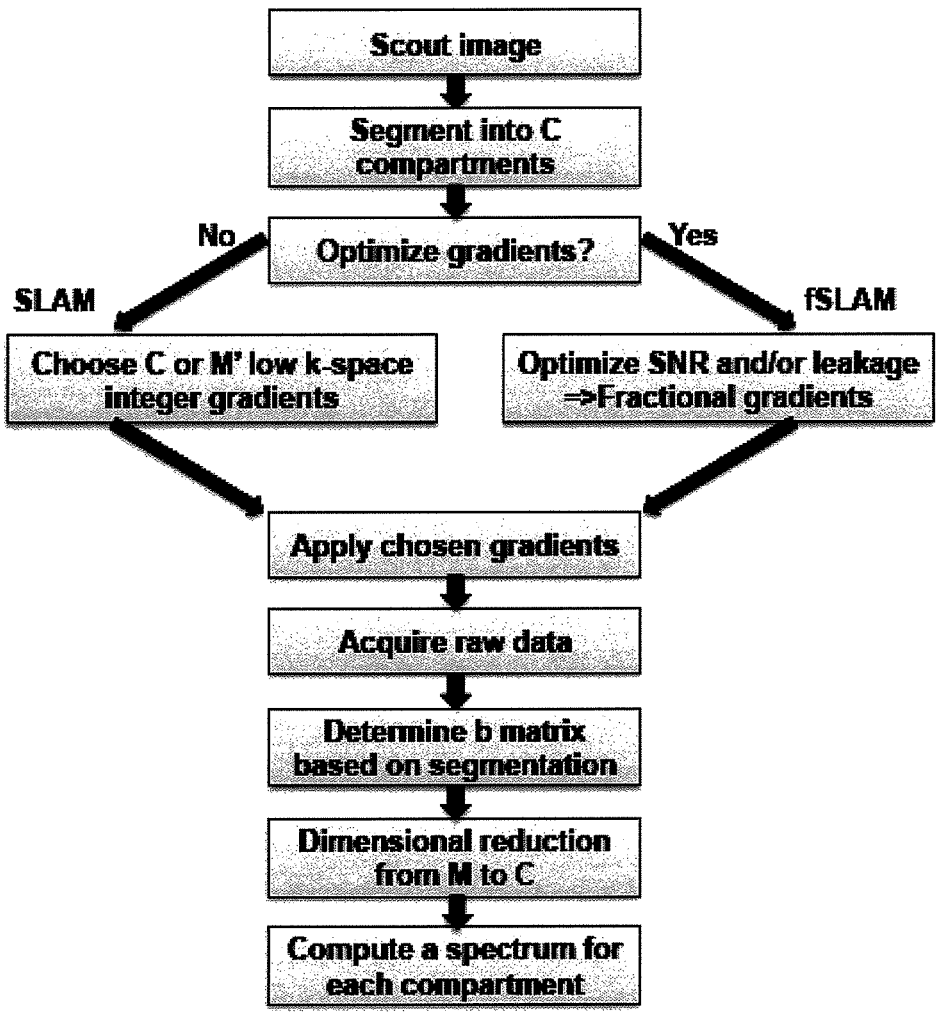
FIG. 2 is a flow chart depicting implementation of the presently disclosed Spectroscopy by the Linear Algebraic Method, SLAM (left pathway), and fractional SLAM, fSLAM (right pathway) according to embodiments of the current invention.

A flow diagram of the reconstruction algorithm appears in FIG. 2.

SLAM with Fractional Gradients (fSLAM)

The choice of the M' phase-encoding steps need not be limited to the original basis set of M CSI steps corresponding to integer k's in Eq. (3). The M' phase-encoding gradients can be chosen to optimize desired properties of the reconstruction. For example, as we now show, the gradients can be optimized to maximize the SNR, and/or minimize the inter-compartmental signal contamination, and/or minimize the intra-compartmental error due to nonuniform signal sources. This effectively involves allowing for fractional k's in the CSI Eq. (3), with all other experimental parameters left unchanged. Unlike SLAM, this fractional SLAM method, denoted fSLAM, does require scanner-side gradient optimization and prescription.

fSLAM with Maximum SNR

To maximize the SNR, Eq. (9) is modified to include noise terms $\varepsilon_{M' \times N}$ in the time-domain signal:

$$\rho_{C \times N}^{r} + \xi_{C \times N} = PE_{C \times M'}^{+} \times (S_{M' \times N} + \varepsilon_{M' \times N}), \quad (10)$$

where $\xi_{C \times N}$ is the noise in the reconstructed spectra. The noise in the time-domain signal and the noise in the spectra are related via the linear transformation, $\xi_{C \times N} = PE_{C \times M'}^{+} \times \varepsilon_{M' \times N}$. Assuming the standard deviation (SD), σ, of $\varepsilon_{M' \times N}$ is constant, the SNR of the spectrum reconstructed from the $i^{th}$ compartment is:

$$SNR_i = \frac{\rho_{C \times N}^{r}(i)}{\left( \sum_{m=1}^{M'} [|PE_{C \times M'}^{+}(i,m)|^2 \times \sigma^2] \right)^{1/2}} \quad (11)$$

where $PE_{C \times M'}^{+}(i,m)$ is the element corresponding to the $m^{th}$ signal. To maximize the SNR of the $i^{th}$ spectrum in Eq. (11), we numerically minimize the cost-function $$\Gamma_i = \sum_{m=1}^{M'} [|PE_{C \times M'}^{+}(i,m)|^2] / I_{cond} \quad (12)$$

where $I_{cond}$ is '1' when the condition number [23] of $PE_{C \times M'}^{+}$, is less than a user-predefined threshold, u, and '0' otherwise. This logic function ensures the equation system is well-conditioned. Minimization of $\Gamma_i$, yields the best SNR of the $i^{th}$ spectrum for the fSLAM experiment, or indeed the SLAM experiment when the gradients in $PE_{C \times M'}^{+}$ are limited to integer steps.

For comparison, the SNR of the CSI experiment is given by:

$$SNR_i^{CSI} = (L_i/M)^{1/2} \cdot \rho_{C \times N}^{CSI}(i)/\sigma \quad (13)$$

where $L_i$ is the size of the $i^{th}$ compartment with average spectrum $\rho_{C \times N}^{CSI}(i)$. Note that the quotient of Eqs. (11) and (13) approximates Eq. (1) for SLAM and fSLAM when multiplied by $\sqrt{M/M'}$ to account for scan-time differences.

fSLAM with Minimum Inter-Compartmental Leakage

So far we have assumed that every compartment is homogeneous. However, spectra in the CSI basis set that deviate from the compartmental averages can generate signals that propagate between and within each compartment following reconstruction. To optimize the fSLAM experiment with M' phase-encoding steps to suppress leakage, Eq. (6) is reformulated to separate the original ρ matrix into an average and an inhomogeneous part:

$$S_{M'\times N} = PE_{M'\times M} \times b_{M\times M}^{-1} \times b_{M\times M} \times (\rho_{M\times N}^{avg} + \rho_{M\times N}^{inhom}) \quad (14)$$

$$= PE_{M'\times M} \times b_{M\times M}^{-1} \times b_{M\times M} \times \rho_{M\times N}^{avg} +$$

$$PE_{M'\times M} \times \rho_{M\times N}^{inhom}.$$

where each row in $\rho_{M\times N}^{avg}$ is an average spectrum of its compartment and each row in $\rho_{M\times N}^{inhom}$ is the deviation of the true spectrum from its compartmental average. For example, assume we have a 3-voxel compartment with single-point spectra with magnitudes [1.1, 1.0, 0.9]. The average spectrum in this compartment will be '1' and the inhomogeneity will be [0.1, 0, −0.1]. Note that by definition the inhomogeneity terms for the same compartment sum to zero.

On the right side of Eq. (14), the first part $$(PE_{M'\times M} \times b_{M\times M}^{-1} \times b_{M\times M} \times \rho_{M\times N}^{avg})$$

satisfies the ideal homogeneity assumption of SLAM, and the second part $(PE_{M'\times M} \times \rho_{M\times N}^{inhom})$ is the source of signal leakage and errors. The solution to Eq. (14) after dimensional reduction is:

$$PE_{C\times M'}^+ \times S_{M'\times N} = \rho_{C\times N}^{avg} + PE_{C\times M'}^+ \times PE_{M'\times M} \times \rho_{M\times N}^{inhom} \quad (15)$$

Clearly, we need to minimize $(PE_{C\times M'}^+ \times PE_{M'\times M} \times \rho_{M\times N}^{inhom})$ to suppress leakage. In the absence of control over $\rho_{M\times N}^{inhom}$, a reasonable strategy is to minimize the coefficients in $PE_{C\times M}^l = PE_{C\times M'}^+ \times PE_{M'\times M}$. Because the inhomogeneity terms in the same compartment sum to zero, their mean can be subtracted. In the example above, if the three coefficients corresponding to inhomogeneity [0.1, 0, −0.1] are [½, ⅓, ⅙], they will generate the same errors as coefficients [⅙, 0, −⅙] after subtracting the mean value of ⅓. This coefficient set has a smaller sum-of-the-squares and is not affected by differences in the mean coefficient of each compartment.

Let $PE_{C\times M}^{ll}(i)$ denote the new matrix of coefficients that results from subtracting the mean from $PE_{C\times M}^{l}(i)$, for each compartment. Then, to minimize the inter-compartmental leakage into the $i^{th}$ compartment, we minimize the sum-of-the-squares of the coefficients in $PE_{C\times M}^{ll}(i)$ that derive from outside of the $i^{th}$ compartment, analogous to SLOOP[5]:

$$\phi_i = \sum_{j\neq i}^{C} \sum_{m\in compartment\ j}^{M} w_{ij} \times |PE_{C\times M}^{ll}(i,m)|^2 \quad (16)$$

Here, $w_{ij}$ is the weight of inter-compartment leakage from the $j^{th}$ compartment into the $i^{th}$ compartment. The $w_{ij}$ can reflect, for example, intrinsic differences in metabolite concentrations between compartments.

Minimizing Intra-Compartmental Errors in fSLAM

To minimize the errors due to inhomogeneity within the $i^{th}$ compartment in the fSLAM experiment, we minimize the sum-of-the-squares of the coefficients that originate from inside of the $i^{th}$ compartment itself:

$$\varphi_i = \sum_{m\in compartment\ i}^{M} w_{ii} \times |PE_{C\times M}^{ll}(i,m)|^2 \quad (17)$$

where $w_{ii}$ is the weight of intra-compartment error in the $i^{th}$ compartment.

To perform a numerical optimization that minimizes both the inter- and intra-compartmental errors, in practice we minimize the cost-function:

$$\Lambda_i = (\phi_i + \varphi_i)/I_{cond} \quad (18)$$

for the $i^{th}$ compartment.

Summary of the fSLAM Method

In summary, the fSLAM experiment is performed using the same Steps 1-5 as the SLAM protocol (FIG. 2) except that the phase-encoding gradients in Step 2 are obtained by minimizing either the SNR cost-function in Eq. (12) or the error cost-function in Eq. (18). In general, the different optimizations will result in different sets of phase-encoding gradients. If a gradient set optimized for both SNR and minimum error is being sought, minimization of the sum of the cost-functions in Eqs. (12) and (18) cannot be used because their scales differ. Instead, minimization of a weighted sum of the ratio of cost functions for fSLAM to those for SLAM can suffice. The choice of the weighting will depend on the application and error tolerance. The phase-encoding gradients in Step 2 are typically fractional.

Because $PE_{C\times M}^{ll}(i)$ is derived from b and therefore requires knowledge of compartment location and size, and the choice of gradients is not constrained to the CSI integer gradient steps, optimization and selection of the fSLAM gradient set must be performed scanner-side as part of the MRS set-up in order to achieve any SNR advantage compared to the summed CSI spectra from the same compartment volume.

Spatial Response Function

In accordance with Eqs. (9) and (12) of references [13] and [24] respectively, we define a spatial response function for the heart compartment corresponding to the row $PE_{C\times M'}^+(h)$ as:

$$SRF_h(x) = \sum_k PE_{C\times M'}^+(h) \cdot \exp(-i2\pi kx). \quad (19)$$

The heart compartment spectrum is $$\rho_h = \int_{FOV} SRF_h(x) \cdot f(x)dx, \quad (20)$$

where f(x) is the true continuous signal. f(x) can be decomposed into signals from chest, $f_c(x)$, and everything else, $f_r(x)$:

$$\rho_h = \int_{chest} SRF_h(x) \cdot f_c(x)dx + \int_{rest} SRF_h(x) \cdot f_r(x)dx. \quad (21)$$

The first integral in Eq. (21) is the chest to heart leakage, ε.

We express $f_c(x)$ as a mean $\bar{f}_c$ plus an inhomogeneity $\Delta f_c(x)$. Then:

$$\varepsilon = \int_{chest} SRF_h(x) \cdot [\bar{f}_c + \Delta f_c(x)]dx \quad (22)$$

$$= \bar{f}_c \cdot \int_{chest} SRF_h(x)dx + \int_{chest} SRF_h(x) \cdot \Delta f_c(x)dx$$

-continued $$\leq \overline{f_c} \cdot \int_{chest} SRF_h(x)dx + \int_{chest} |SRF_h(x)| \cdot |\Delta f_c(x)|dx$$

$$\leq \overline{f_c} \cdot \int_{chest} SRF_h(x)dx + \max(|\Delta f_c(x)|) \int_{chest} |SRF_h(x)|dx$$

The right hand side of the last line of Eq. (22) is the upper limit of the contamination of the heart spectrum from chest signal.

Methods

Computer Simulations

Figures 3A, 3B, 3C, 3D:
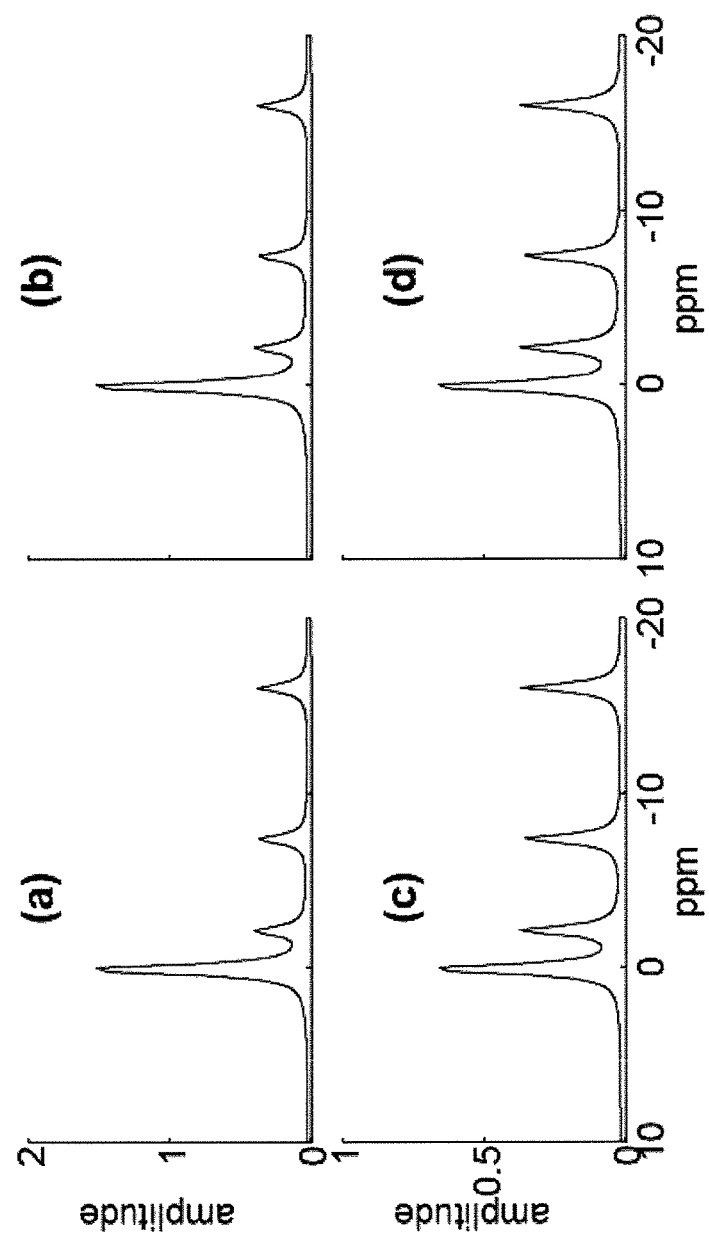
FIGS. 3A-3D show simulated 16-step phosphorus ($^{31}$P) one-dimensional (1D) CSI spectra of a model chest with 3 skeletal muscle voxels (3A) and 4 heart voxels (3C). The reconstructed SLAM chest (3B) and heart (3D) spectra are indistinguishable from the originals.

Computer simulations were performed to investigate the accuracy of SLAM as applied to human cardiac $^{31}$P MRS, where 1D CSI has served as a work-horse in our laboratory [17-21]. Three compartments were assumed: the heart, chest skeletal muscle, and 'other'. In practice, the 'other' compartment is needed because any signal generated outside of the designated compartments that is not assigned a compartment, will end up in the chest and heart, introducing errors depending on its magnitude. The chest and heart spectra are shown in FIGS. 3A, 3C. Signals are generated from these spectra with predefined compartment distributions using a 16-voxel 1-cm resolution 1D CSI model.

Figures 4A, 4B, 4C, 4D, 4E:
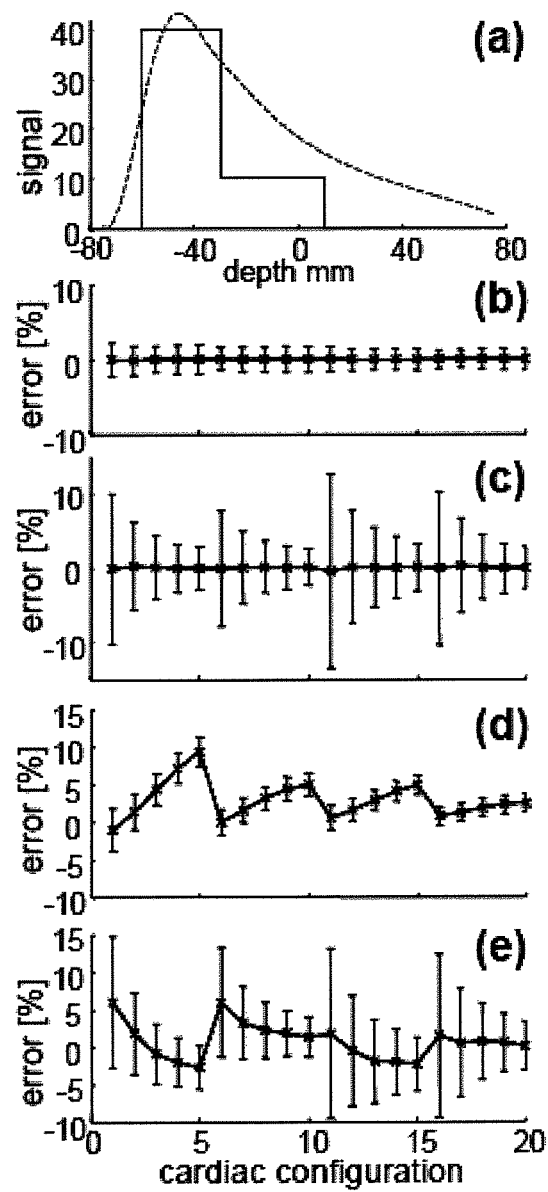
FIGS. 4A-4E show cardiac model (4A) and Monte Carlo simulation of the effect of noise and 30% (±15%) inhomogeneity on the accuracy of SLAM signal reconstruction vs. CSI (4B-4E). The chest-to-heart signal ratio is held constant at 4 in (4B, 4C) depicted by the dark continuous curve in (4A). In (4D, 4E) the ratio is 2.5 scaled by the experimental surface coil sensitivity profile depicted by the blue dashed curve in (4A). Errors are mean±SD (standard deviation) in the chest (4B, 4D) and heart (4C, 4E), calculated with cardiac signal-to-noise ratio, SNR=20. The largest errors in the heart correspond to configurations #1 (2 cm chest, 2 cm heart, no separation between chest and heart), #6 (2 cm chest, 2 cm heart, 1 cm gap), #11 (3 cm, 2 cm, 0 cm), and #16 (3 cm, 2 cm, 1 cm).

Monte Carlo simulations were done to quantify errors in SLAM arising from imperfections in the homogeneity assumption for this model. Based on experience[17-20], we assumed a metabolite-bearing chest muscle thickness of 2-3 voxels, a heart muscle thickness of 2-6 voxels, and zero or a single voxel separation between the chest and heart compartments, and zero signal in the 'other' compartment. This yielded 20 possible anatomical combinations. To accommodate the combined effect of differences in concentration and surface coil sensitivity, two scenarios were investigated. In the first, we assumed a constant chest to heart signal ratio of 4. In the second, we assumed a chest PCr concentration 2.5 times higher than heart[21], and scaled the result by the experimental surface coil spatial sensitivity profile as shown in FIG. 4A. A random inhomogeneity of ±15% (30% total) in the resultant signal was then simulated for both scenarios. The mean signal was determined for each compartment by adding signals from the corresponding voxels of the full CSI set to serve as a reference. Then, white noise was added such that the SNR in the heart compartment was 20. The FT of the data set was used to generate a set of time-domain CSI acquisitions from which the M'=4 central k-space acquisitions were selected. SLAM reconstruction from these 4 phase-encoding steps was implemented, and the percentage error relative to the reference CSI value was calculated. The mean error and the SD of the error were determined after 1000 Monte Carlo simulation runs.

Monte Carlo simulations were also performed to compare the sensitivity of SLAM with SLIM[3], with respect to registration errors. A 1D cardiac $^{31}$P model with chest from −60 mm to −30 mm, heart from −30 mm to 10 mm, and a chest-to-heart signal ratio of 4 was assumed as in scenario-1, above (FIG. 4A). A random segmentation error between −2 mm and +2 mm was introduced at the edges of either compartment: (i) with the chest and heart stationary (no partial volume error); and (ii) with the chest and heart also moved by ±2 mm (partial volume error). The chest was constrained never to overlap the heart. Both SLAM and SLIM were simulated with four CSI phase-encodes from central k-space. SLIM reconstruction was performed as prescribed[3], by integrating the phase-encoding coefficients over the 3-compartment model of heart, chest and 'other' and generating a 4×3 'G'-matrix[3]. The mean (±SD) % error between the reconstructed signal and the true or the CSI result was calculated for 1000 runs.

The SNR and the root-of-the-sum-of-the-squares of the inter- and intra-compartment errors, $\sqrt{\phi_i + \phi_j}$, were computed for the model heart, assuming 3- and 4-voxel cardiac compartments and a 2-voxel chest compartment for both SLAM and (SLAM, and that both techniques yield the same compartmental average. The SNR was measured relative to the compartment average SNR of the 16-voxel 1D CSI (Eq. (13)), using the M'=3 to 16 central k-space acquisitions for SLAM, and fractional (low k-space) phase-encodes for (SLAM. Optimization was performed using the simplex method implemented via the Matlab "fminsearch" routine (The MathWorks, Natick, Mass.) on a lap-top computer with a threshold u=50 for Eqs. (12) and (18), and with all the leakage weighting factors, $w_{ij}$ set to '1' in Eqs. (16) and (17).

$SRF_h$ was calculated from Eq. (19) for 4-step SLAM, 4-step fSLAM, 16-step CSI and 4-step CSI (zero-filled to 16 steps) for the 3-voxel chest/4-voxel heart model. The upper bound of chest contamination of the heart spectrum for the four cases was calculated from Eq. (22) assuming an effective chest to heart ratio of 4 and an intra-compartmental inhomogeneity of ±15% (30% total) for the chest.

Experiments $^{31}$P 1D CSI, SLAM, and fSLAM were implemented in a 3T Philips Achieva MRI/MRS system on phantoms, the human leg, and the human heart. The phantom studies were done with a 14-cm diameter single loop transmit/receive coil, and the human studies used a 17-cm/11-cm diameter dual loop transmit and a 8-cm diameter single loop receive $^{31}$P coil set described previously[22]. All human studies were approved by the Johns Hopkins Medicine Institutional Review Boards and all participants provided informed consent. The individual CSI spectra from all of the volume elements constituting each compartment were co-added post-acquisition for all comparisons of spectra from the equivalent volumes reconstructed using SLAM and fSLAM.

Phantom studies were performed on two standard Philips $^{31}$P test disks 15-cm in diameter and 2.5-cm thick. One contained 300 mM $H_3PO_2$, the other had 300 mM $H_3PO_4$. A standard 1D CSI protocol using frequency-sweep-cycled (FSC) adiabatic half passage (AHP) pulses was applied (field-of-view, FOV=160 mm; voxel/slice thickness, SL=10 mm; repetition time, TR=6 s; CSI phase-encoding steps, k=−8, −7, −6, −5, −4, −3, −2, −1, 0, 1, 2, 3, 4, 5, 6, 7; acquisition delay, 1.4 ms) [22]. The SLAM protocol (FIG. 2) was then implemented with the same CSI parameters except for the phase-encoding gradients, which were reduced to a subset of 4 of the same steps (−2, −1, 0, 1). A 3-compartment model comprised of the two disks plus an 'other' compartment was assumed.

The leg was studied with the 300 mM $H_3PO_4$ disk phantom on top to create an additional compartment. 1D CSI was first performed with FSC AHP excitation (FOV=160 mm; SL=10 mm; TR=8 s; phase-encoding steps, k=−8, −7, . . . , 7). This was followed by SLAM with the same total scan time and gradient-step increments but using only the 4 central k-space steps (−2, −1, 0, 1 repeated 4 times).

Human cardiac $^{31}$P MRS studies comparing SLAM and CSI were performed on 8 normal volunteers and 16 patients with non-ischemic cardiomyopathy using the same protocol (FOV=160 mm; SL=10 mm; TR=15.7 s, cardiac triggered). For each subject, CSI data reconstructed from all 16 phase-encoding steps, was compared with SLAM reconstruction employing only the middle 4 phase-encoding steps of the same CSI data sets. This effectively reduced the scan time by 4-fold. The effect of using just 2 phase-encoding steps from central k-space corresponding to chest and heart compartments only, was also investigated. The resulting spectra were fit by the circle-fit method[25] to provide a quantitative comparison of PCr and γ-ATP peak areas measured by SLAM with those from conventional CSI (the localization and spectral analysis method are independent). Spectra were exponential-filtered (15-Hz line-broadening) and zero-filled 4 times to 2048 points.

The performance of fSLAM with respect to SNR and compartmental leakage was compared with that of CSI and SLAM in proactive cardiac $^{31}$P MRS studies of 6 additional healthy volunteers. Sequentially, a first CSI, a SLAM, an fSLAM, and a repeat last CSI scan were acquired from each subject. CSI utilized the standard 16 phase-encoding steps from −8 to 7 (FOV=160 mm; SL=10 mm; TR=15.7 s, cardiac triggered). SLAM used the same 4 middle k-space phase-encoding steps for each exam, repeated four times for the same total scan-time as CSI. fSLAM phase-encoding employed 4, typically-fractional gradient steps, specifically optimized for minimum compartmental leakage in the heart compartment for each volunteer, after manual segmentation of the scout MRI using the scanner's cursor function. As in the simulations, optimization was performed using Matlab on a lap-top computer at the scanner-side, with weighting factors set to unity. The four gradient values were manually entered as experimental parameters in the fSLAM pulse sequence on the scanner. The four steps were repeated four times for the same total scan-time as the CSI.

Results

Computer Simulations

FIGS. 3A-3D show that SLAM spectra of the chest and heart, reconstructed using only the three middle (k-space) phase-encoding steps of the original 16, are indistinguishable from the original simulated spectra in the absence of inhomogeneity or noise. The effect of adding noise and inhomogeneity on SLAM spectra reconstructed for a range of different chest-muscle and heart compartment distributions, is illustrated by the Monte Carlo simulations for both models of concentration and sensitivity variations in FIGS. 4A-4E. These show that the accuracy of the reconstruction, as indexed by the mean of the error <10% for all chest/heart anatomical combinations. As might be expected, the higher the concentration or larger the compartment size, the smaller the error SD. For the heart, the simulations predict highest errors when the effective extent of the cardiac compartment is smallest.

The effect of small errors in the registration of compartments for CSI, SLAM and SLIM, as compared to the true value and to CSI, are summarized in Table 1. The Monte Carlo simulations show that small segmentation errors of just ±2 mm can introduce random errors approaching 10% for SLIM when the object is stationary, while SLAM is virtually unaffected and is less sensitive to partial volume errors. SLAM's relative insensitivity to small segmentation errors is critical for real applications since perfect segmentation is rarely possible in practice, especially in cardiac $^{31}$P MRS.

TABLE 1

Monte Carlo analysis of the effect of ±2 mm misregistration on accuracy of cardiac PCr measurements for a 30 mm chest/40 mm heart model.

| | Error (mean ± SD), % | | |
|---|---|---|---|
| Simulation (1000 runs) | CSI | SLAM | SLIM |
| With model fixed on CSI grid, error vs. true | 2.7 ± 0.0 | 0.7 ± 0.0 | 1.1 ± 8.4 |
| With ±2 mm partial volume shift, error vs. CSI | 0.0 ± 0.0 | −2.2 ± 5.1 | −1.1 ± 9.8 |
| With ±2 mm partial volume shift, error vs. true | 2.4 ± 5.2 | 0.3 ± 8.2 | 1.1 ± 8.7 |

Figures 5A, 5B, 5C, 5D:
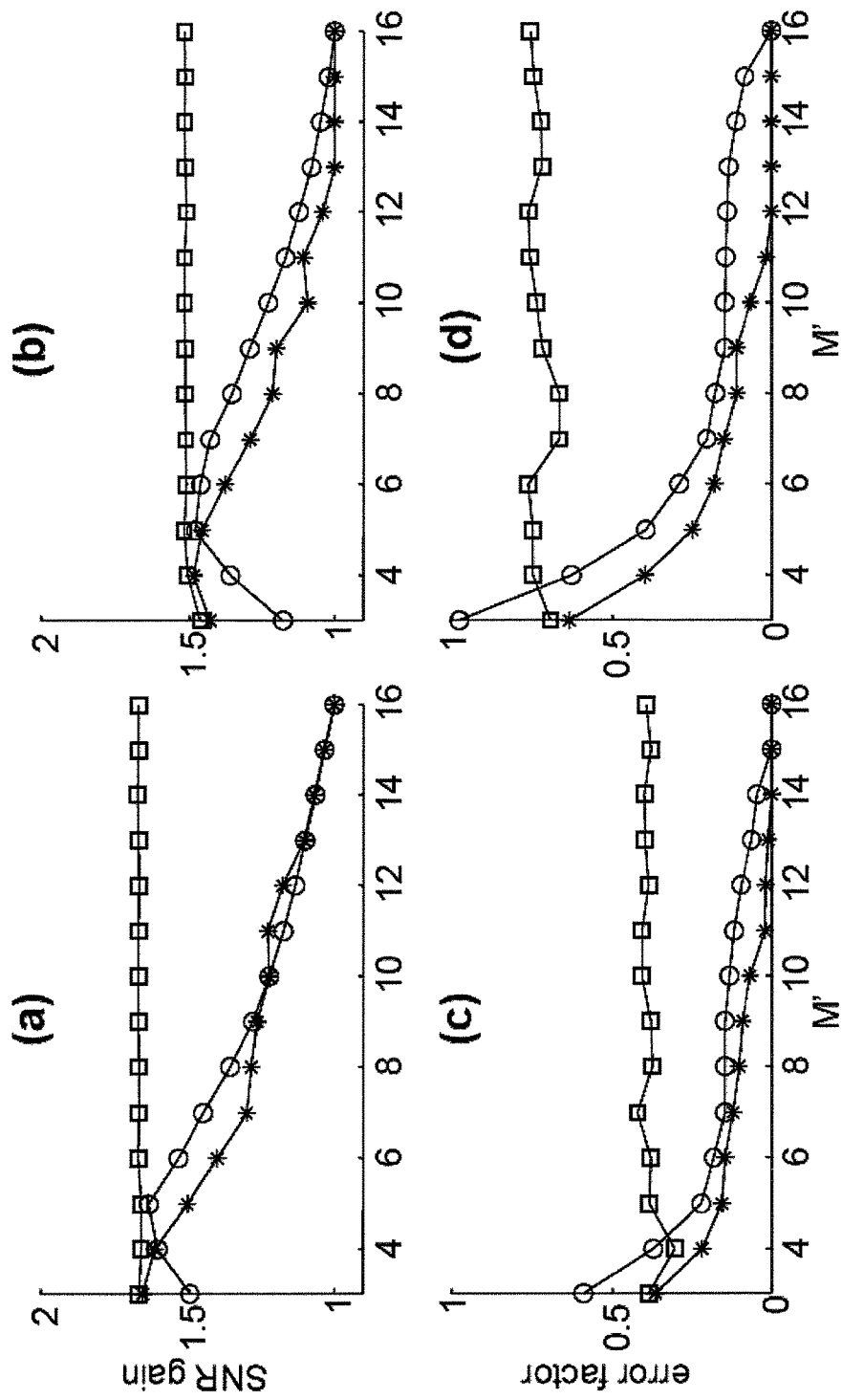
FIGS. 5A-5D show the SNR gain for the same volume (5A, 5B), and the total inter- and intra-compartment error factor, $\sqrt{\phi_I + \phi_i}$, (5C, 5D) for SLAM and fSLAM in the heart as a function of the number of phase encodes, M', of the original M=16 that are allowed. For comparison, CSI has an SNR=1 with zero error assumed. Points depict results for three sets of gradients (square points, fSLAM with maximum SNR; stars, fSLAM with minimized inter/intra-compartmental errors; circles, SLAM). Here, (5A) and (5C) are for a 4-voxel thick heart; (5B) and (5D) are for a 3-voxel-thick heart compartment, all with a 2-voxel thick chest compartment.
Figures 6A, 6B, 6C, 6D:
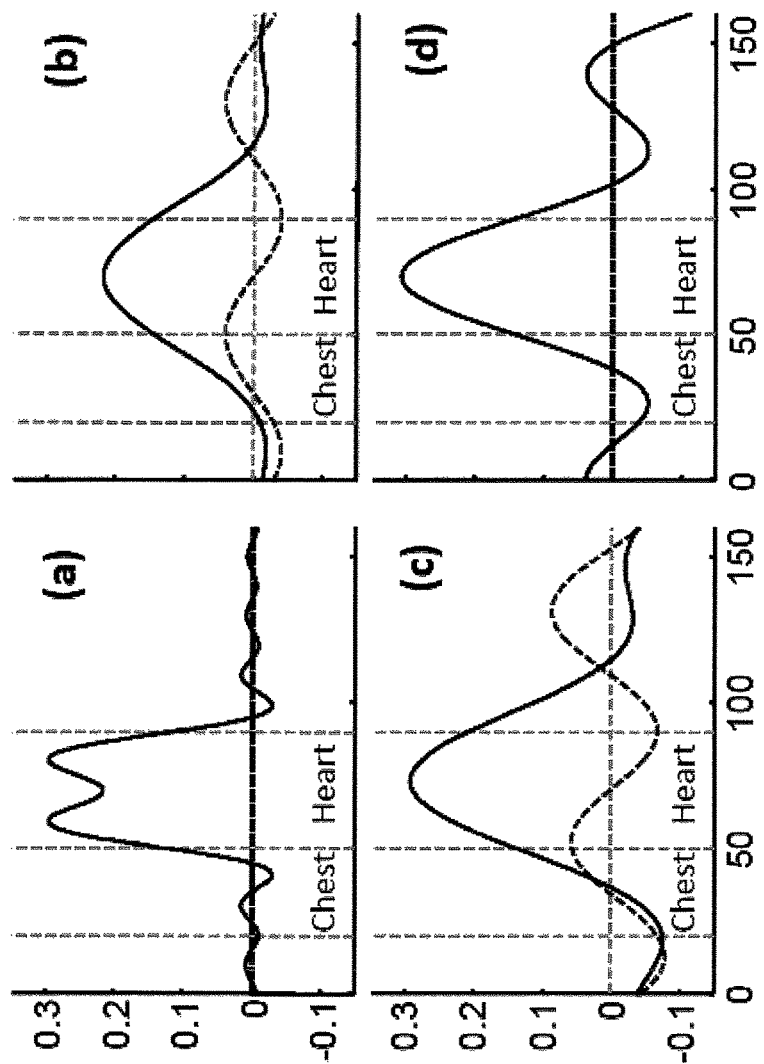
FIGS. 6A-6D show the spatial response function for the heart compartment, $SRF_h$, for (6A) 16- and (6B) 4-step CSI (zero-filled to 16 steps), (6C) 4-step SLAM and (6D) 4-step fSLAM, computed for a model comprised of 3 chest voxels adjoining 4 heart voxels (black lines, real part; dashed red, imaginary component). Vertical dashed lines delineate the chest and heart compartments, as labeled. The signal contribution from each compartment derives from the integral of the curve over that compartment.

The results of the analysis of SNR gain and the combined inter- and intra-compartment error factor, $\sqrt{\phi_i + \phi_j}$, for SLAM and fSLAM, as compared with 16-voxel 1D CSI of the heart, are shown in FIG. 5 with 3- and 4-voxel thick cardiac compartments. The maximum SNR results from choosing the phase-encoding steps closest to central k-space. Because SLAM is confined to the CSI's integer phase-encoding set, its SNR advantage fades as more-and-more of the high k-space phase-encodes are used. Optimum SNR performance for SLAM occurs when the number of phase-encodes approximates the number of compartments, wherein its performance approximates that of fSLAM. Thus for SLAM, the best strategy is to choose the M'≈C non-equal CSI phase-encoding steps at or closest to the center of k-space, and repeat or average the acquisitions up to the allotted scan time, rather than add any higher k-space phase-encodes. On the other hand, fSLAM always achieves 1.5-1.8 times the SNR of standard CSI independent of the number of phase-encoding steps that are allowed. This reflects the fact that fSLAM is free to choose an array of fractional phase-encodes that all fall close to central k-space. For fSLAM, the additional phase-encodes offer the added benefit of reduced signal bleed (FIGS. 5C, 5D). The errors, $\sqrt{\phi_i + \phi_j}$, for fSLAM decay faster than SLAM as phase-encodes are added, indicating better error suppression, with larger compartments generating less error than smaller ones.

FIGS. 6A-6D plots SRF$_h$ for 16- and 4-step CSI, 4-step SLAM and 4-step fSLAM. It is important to recognize that the signal derives from the integral of the curve over each compartment, resulting in cancellation of signal outside the heart. When the chest signal is uniform, the cancellation is essentially perfect in the case of SLAM and fSLAM but not CSI (Table 2, first row). When the signal in the chest compartment varies by up to 30% peak-to-peak, the upper bound for contamination of the heart compartment rises to 12-14% for SLAM and fSLAM. This compares to 9% for 16-step CSI, while the 4-step CSI is basically unusable (Table 2, second row).

TABLE 2

Integral of SRF$_h$ and upper bound of chest contamination for CSI, SLAM and fSLAM$^a$

| | 16-step CSI | 4-step CSI | SLAM | fSLAM |
|---|---|---|---|---|
| Integral of SRF$_h$ over chest | 0.0138 | 0.1654 | 0.0045 | 0.0073 |
| Upper bound of ε$^b$ | 9.0% | 77.3% | 13.9% | 12.0% |

$^a$Computed for 3-slice chest/4-slice heart model.
$^b$Computed with chest/heart signal ratio of 4 and ±15% (total 30%) chest inhomogeneity.

Experiments

Figures 7A, 7B, 7C, 7D, 7E:
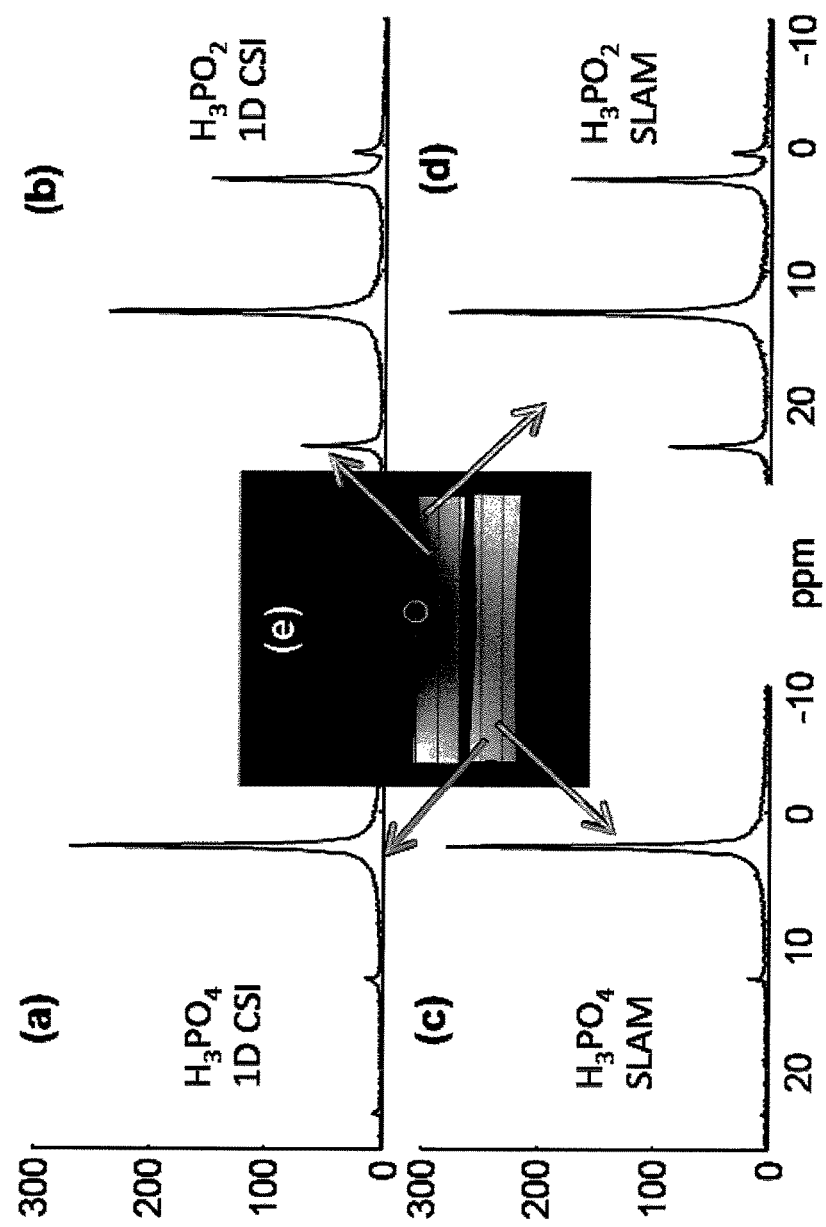
FIGS. 7A-7E show CSI and SLAM spectra reconstructed from the standard Philips Medical System's $^{31}$P test phantom comprised of a H$_3$PO$_4$ disk on the bottom (7A, 7C), and a H$_3$PO$_2$ disk on top (7B, 7D), as shown in the image (7E). The CSI spectra (7A, 7B) are the sum of the spectra from the voxels (red horizontal lines) containing the disks and were acquired with 16 phase-encoding gradients (−8 . . . +7). The SLAM spectra (7A, 7D) were acquired 4-times faster with just 4 phase-encodes (−1, −2, 0, 1). The SNR for the CSI spectra are 660 (7A) and 638 (7B), compared to 528 (7C) and 482 (7D) for SLAM. The signal at ~0 ppm is a contaminant present only in the H$_3$PO$_2$ disk.

Spectra from the two-disk inorganic phosphate phantom reconstructed using CSI and SLAM are shown in FIG. 7. $H_3PO_4$ has a single $^{31}P$ peak at 2.9 ppm, while the $H_3PO_2$ resonance is a triplet centered about 13.5 ppm (coupling constant, 545 Hz), due to heteronuclear coupling with hydrogen. Despite the 4-fold reduction in scan-time, the SLAM spectra from the two disks are very similar to the summed CSI spectrum from the same compartment volumes, with negligible leakage consistent with the simulations (FIG. 4).

Figures 8A, 8B, 8C:
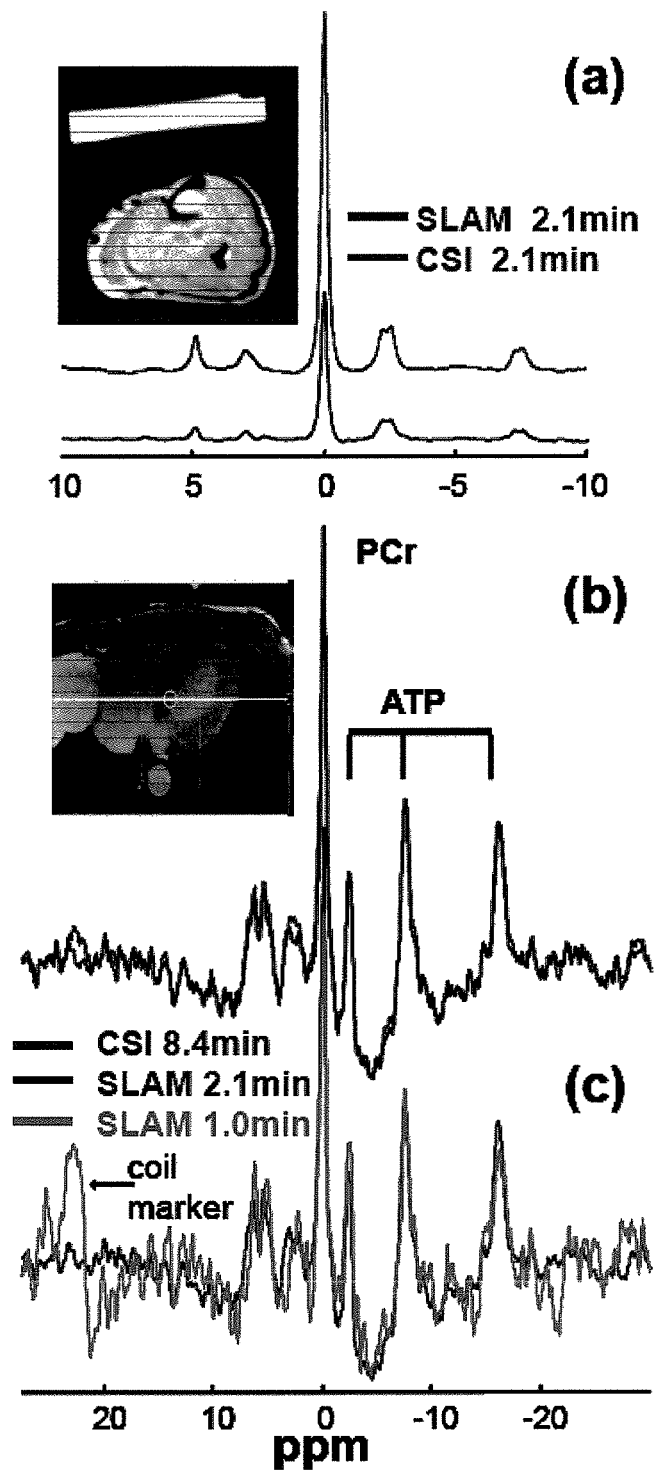
FIGS. 8A-8C show (8A) human leg $^{31}$P spectrum acquired by SLAM (top) and CSI (lower) from the same 6-voxel volume in the same scan time (2.1 min).

Spectra from the same-sized leg compartment obtained by CSI (averaging n=6 voxels) and SLAM (same volume) are presented in FIG. 8A normalized to constant noise. The SLAM spectrum has 2.1 times better SNR than CSI, and shows negligible signal contamination or bleed from the $H_3PO_4$ phantom positioned above the leg. FIG. 8B shows $^{31}P$ heart spectra from a 16-step 1D CSI (averaging 4 voxels), 4-step SLAM and 2-step SLAM from the same volume. The baseline roll is due to the acquisition delay for the phase-encoding gradient. Again, negligible bleed is evident in the 4-step SLAM spectrum, either from adjacent chest skeletal muscle or from an embedded coil marker (at ~23 ppm). Importantly, while the reproducibility and SNR of CSI and SLAM are comparable here, the SLAM spectrum was acquired 4-times faster. Even with only two steps, the SLAM reconstruction remains surprisingly good as shown in FIG. 8C. With 2 phase encodes, just two signal-generating compartments, chest muscle and heart, are allowed, resulting in some signal bleed from the external coil marker in a spectrum acquired 8-times faster than the CSI standard.

Figures 9A, 9B, 9C, 9D:
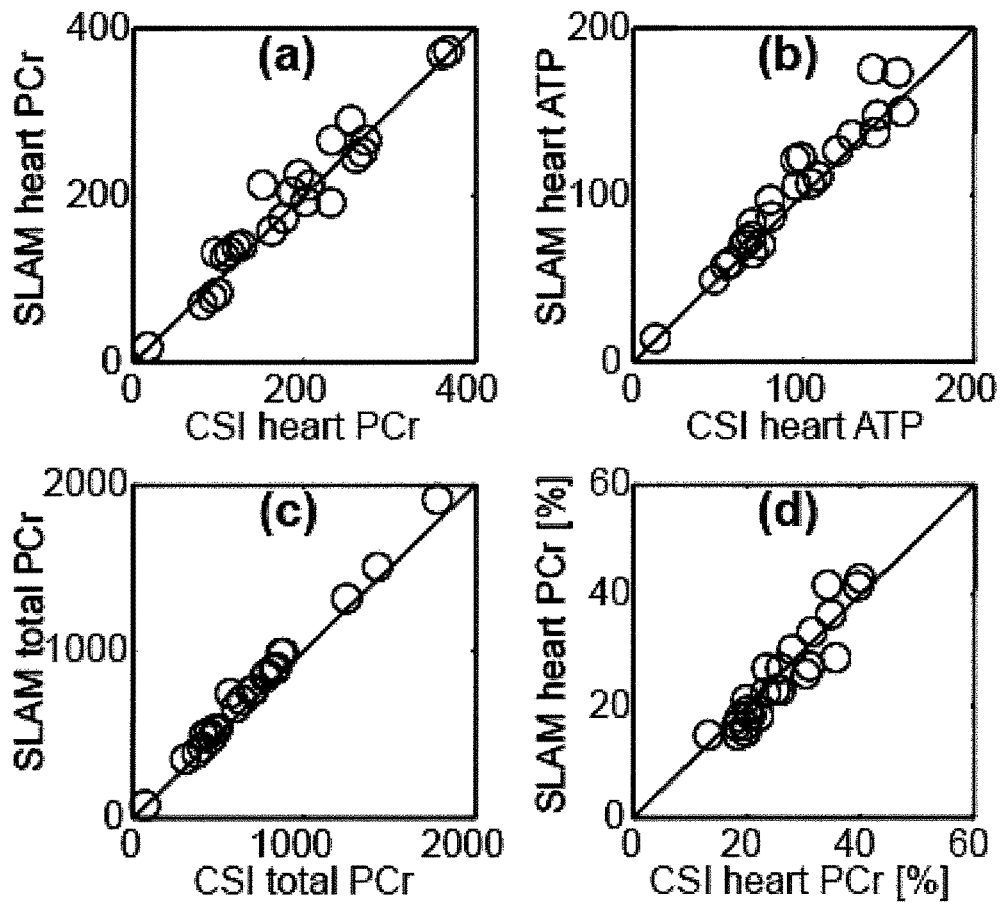
FIGS. 9A-9D show fitting results reconstructed by SLAM from a subset of 4 of the 16 CSI phase encoding steps acquired from the 24 heart patients and control subjects, as compared to the CSI results. (9A) Phosphocreatine, PCr, and (9B) gamma-phosphate of adenosine triphosphate, γ-ATP, peak areas quantified in the cardiac compartment. (9C) The total PCr from both heart and chest compartments. (9D) The ratio of heart PCr to the total PCr from both chest and heart compartments. The correlation coefficients are r>0.97 in all cases, and the solid line is the identity line.

The comparison of fitting results from the cardiac 4-step SLAM and 16-step CSI spectra from 8 healthy subjects and 16 patients are presented in FIG. 9. In these data sets, the ratio of PCr signal in chest to that in heart compartments was at or below ~5. The PCr and γ-ATP peak areas from the SLAM reconstruction agree with those from CSI reconstruction (FIGS. 9A, 9B). The myocardial PCr/ATP ratio for the pooled patients and healthy subjects was the same (1.94±0.60 in CSI vs. 1.90±0.67 in SLAM), consistent with negligible contamination from chest muscle with its much higher PCr/ATP ratio of ~4[19]. The data also show that the total of the PCr in the chest plus that in the heart compartments measured by SLAM, is equal to the total measured by CSI (FIG. 9C). Thus, the total signal is conserved. Furthermore, the fraction of cardiac PCr to the total PCr measured by SLAM is also equal to that measured by CSI (FIG. 9D). This means that the contamination of heart spectra from chest muscle in SLAM is not distinguishable from that in CSI. This result is consistent with Table 2. Importantly, all these SLAM results correspond to acquisitions effectively taking $\frac{1}{4}^{th}$ of the scan-time of CSI.

Figures 10A, 10B, 10C, 10D:
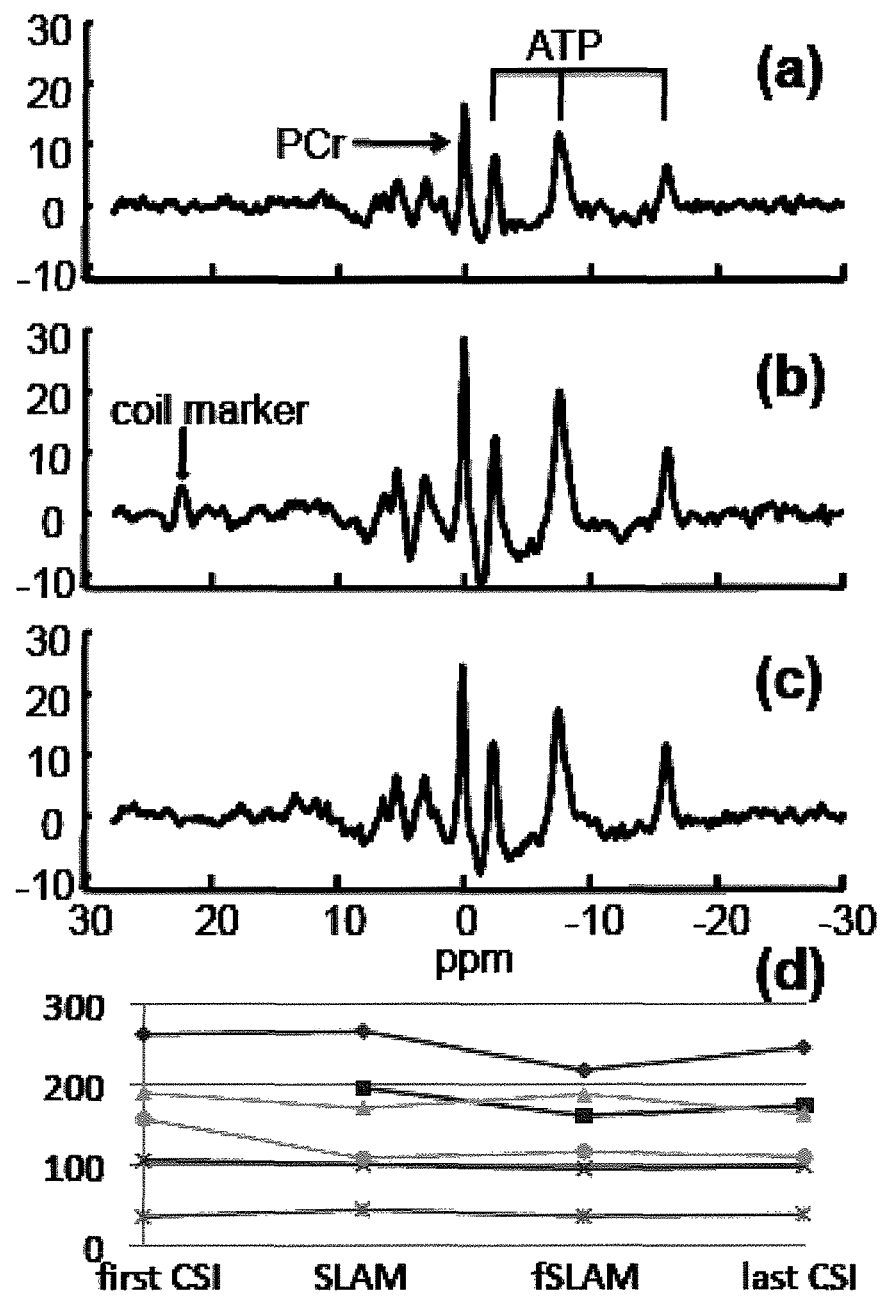
FIGS. 10A-10D show (10A) CSI, (10B) SLAM and (10C) error-minimized fSLAM spectra, all normalized to constant noise on the same volunteer with the same total scan time and total voxel volume. Gradient encoding steps of −8 to +7 (integer) were used for standard CSI; integer steps −2, −1, 0, 1 repeated 4 times were used for SLAM; and fSLAM used non-integer steps −2.13, −0.73, +0.73, +2.13 repeated 4 times. (10D) Cardiac PCr peak area from proactive $^{31}$P MRS studies of all 6 subjects in the first CSI, the SLAM, the fSLAM and the repeated CSI scan (no significant difference between exams at paired t-testing; lines connect measurements from the same subjects).

FIGS. 10A-10D compare CSI, SLAM and fSLAM $^{31}P$ cardiac spectra proactively acquired in the same total scan-time from the same volume size in the same healthy volunteer. The time taken to implement fSLAM scanner-side was 1-2 min to manually segment the scout MRI, plus several seconds to optimize the gradient set on the lap-top computer. The SLAM and fSLAM spectra both have higher SNR than CSI from the same volume, while a possible bleed signal from the coil marker in the SLAM spectrum is absent in the fSLAM spectrum. Table 3 lists the SNR of human cardiac PCr in same-sized voxels for CSI, SLAM and fSLAM in 6 volunteers acquired in the same scan time. The mean SNR improvement for SLAM vs CSI for the six studies is 1.42±0.23. The mean SNR improvement for fSLAM vs CSI for the six studies is 1.34±0.19. According to Eq. (1), this SNR gain would be consistent with a cardiac compartment equivalent to two of the 1-cm CSI voxels even though the reconstruction assumed a 4-voxel cardiac compartment. This likely reflects the combined effect of the decline in surface coil sensitivity with depth, and the 1-2 cm thickness of the anterior myocardial wall. As in FIG. 9, there is no evidence of chest muscle contamination of either the SLAM or fSLAM spectra. The PCr/ATP ratio for SLAM and fSLAM was not significantly different from that measured in either the first or the repeated last CSI scans, and the absolute metabolite signal levels do not change (FIG. 10D).

TABLE 3

The cardiac $^{31}P$ MRS SNR of PCr for the same cardiac voxel volumes and scan time using CSI, SLAM, and fSLAM in n = 6 healthy volunteers (left-to-right).

|  | Vol 1 | Vol 2 | Vol 3 | Vol 4 | Vol 5 | Vol 6 | Average |
|---|---|---|---|---|---|---|---|
| CSI | 61 | 30 | 33 | 18 | 18 | 26 | 31 ± 16 |
| SLAM | 86 | 53 | 41 | 30 | 20 | 39 | 45 ± 23[a] |
| fSLAM | 71 | 45 | 44 | 32 | 21 | 31 | 41 ± 17[b] |

[a]$p < 0.01$ vs. CSI, paired t-test.
[b]$p < 0.002$ vs. CSI, paired t-test.

Discussion

Single voxel methods such as PRESS[26], STEAM[27] or ISIS[28] are good localization choices for performing MRS of a single compartment, but do not offer optimum SNR for a fixed scan time for MRS of multiple compartments. In addition, their sensitivity to relaxation effects (both $T_1$ and $T_2$) and motion, presents real problems for quantification, especially in $^{31}P$ MRS[1, 26]. CSI, being a simple pulse-and-acquire experiment that collects all-of-the-signal from all-of-the-sample, all-of-the-time, currently offers the cleanest approach to quantitative MRS, with potentially the highest SNR efficiency. It is however, limited by the minimum scan-time required to encode the entire sensitive volume or FOV of the detector coil. This can limit the direct translation of SNR gains, such as those afforded by higher $B_0$ magnetic field strengths, to reductions in scan-time.

In addition, the highest SNR efficiency of CSI is only realized when the spatial resolution imposed at the time of acquisition, matches the desired compartment size[1]. Unfortunately, CSI's spatial resolution is usually set not by the size of the desired compartment, but by the geometry of the tissue that it must be distinguished from (eg, the chest in heart or liver studies, the scalp in brain studies). Alternative approaches that localize spectra to pre-selected compartments based on anatomical MRI information, are not new. The SLIM, GSLIM and SLOOP methods were originally proposed some 20 years ago[3-5], but see little use today compared to CSI or even PRESS, STEAM or ISIS. When SLIM, GSLIM and SLOOP are applied to regular CSI acquisitions, without pro-active implementation or gradient selection criteria that place a premium on SNR—as is most often the case[3, 4, 6-16], they cannot deliver the highest SNR achieved by matching the resolution to the compartment, a priori. Although not previously documented, the difference, ~g in Eq. (1), would be significantly higher than the SNR gained from summing signals from the constituent CSI voxels. Similarly, a many-fold speed-up in the minimum CSI scan-time could result if the phase-encoding gradient set were cut.

Here for the first time we have exploited differences in volume sizes between desired MRS compartments and CSI resolution, to realize and document a g-fold SNR gain consistent with Eq. (1), using a new MRS localization method, SLAM. SLAM differs from SLIM, GSLIM and SLOOP in both the pulse sequence that is applied, and in MRS reconstruction. Simply put and unlike other methods, the SLAM pulse sequence is based on a CSI sequence from which essentially all of the high-order gradient phase-encoding steps are eliminated except for the C phase-encoding steps closest to central k-space. Because the CSI gradient set is discretized, this means that the only a priori information needed to run the sequence is the number C, which is generally fixed for a given study protocol. Compared to pro-active implementation of SLOOP[5], this has the advantage of avoiding image-guided gradient optimization, prescription, and implementation at the scanner-side prior to acquisition. On the other hand, SLIM and GSLIM utilize standard CSI sequences [3, 4, 6, 11, 12].

Like prior methods, reconstruction of SLAM spectra does require a scout MRI to identify and segment the compartments which are assumed uniform. However, SLAM reconstruction differs from SLIM, GSLIM and SLOOP in that it solves a set of C linear simultaneous equations by eliminating un-needed phase-encoding steps from the standard CSI algorithm. SLAM aims to generate spectra that are at best equal to the compartmental average CSI spectra, whereas SLIM, GSLIM and SLOOP use MRI-based constrained reconstruction or SRF optimization to obtain optimally-localized compartment spectra. Because of the relatively coarse resolution of CSI, this renders SLAM relatively insensitive to registration errors in segmenting the compartments-compared to SLIM for example (Table 1), where problems were noted previously[11, 29].

With SLAM, we demonstrate many-fold reductions in the minimum scan-time compared to CSI in theory (FIG. 5) and in practice (FIGS. 8, 9), and substantial SNR gains in human in vivo studies on a standard clinical MRI/MRS scanner operating at 3 Tesla (FIG. 10, Table 3). Importantly, in 1D 31P human cardiac applications, SLAM delivers qualitative and quantitative results (FIG. 10) that are practically indistinguishable from results obtained from conventional CSI, other than being 4-times faster or higher in SNR (FIGS. 3, 7-10). Even so, significant inter-compartmental contamination may arise when signals from adjacent compartments differ greatly or are not segmented. This can occur in $^{31}P$ MRS heart studies, for example, when chest skeletal muscle compartment signals are many-fold higher (eg >5-fold) than cardiac signals due to the higher muscle metabolite concentrations, and/or its thickness, and/or proximity to surface coil detectors with nonuniform sensitivity. Conventional CSI, used here as a standard, is not immune from this problem [30] (Table 2). Despite the uniform compartment assumption, both the numerical results (FIG. 4, Tables 1, 2) and the experiments (FIGS. 7-10) suggest that SLAM is relatively robust to the variations in signal that arise in practical applications such as cardiac surface-coil MRS.

The SLAM acquisition pulse sequence with integer k-space phase-encodes was surprisingly simple to implement, at least for the 1D case. For our cardiac $^{31}P$ MRS studies, we chose the same 4 central gradient steps to provide a fixed SLAM acquisition sequence suitable for up to 4 compartments, extracted from a standard 16-step CSI sequence with the other 12 steps discarded. Further reductions in C and the number of phase-encodes—to 2, for example (FIG. 8C)-risk leakage from unaccounted for signal sources that lie outside of the designated compartments. This may be tolerable if the leakage does not interfere with the spectral region of interest. For validation or test purposes, SLAM can be performed retroactively on raw data sets that are accompanied by a scout MRI, simply by applying the algorithm to a subset of frames in each CSI data set. The result can be compared with the summed CSI from the same-sized compartments analogous to FIG. 9.

fSLAM extends SLAM by removing the limitation that the phase-encodes be selected from the set of integer-stepped CSI gradients. Instead, they are adjusted to minimize leakage or errors due to inhomogeneity and/or maximize SNR. We observed that maximizing SNR alone can produce unacceptable error if the clustering of phase-encodes at the center of k-space is unchecked (FIG. 5). Minimization of inter- and intra-compartmental errors alone yields acceptable results, albeit at the expense of a small reduction in SNR (FIG. 10; Table 3). Thus, inter- and intra-compartmental error was substantially eliminated with fSLAM, also using only four phase-encoding gradient steps. When SNR is low also, inter-compartmental leakage could become problematic relative to the compartment signal. Adjustment of the weighting factors in Eq. (18) from the values of unity used herein may help attenuate bleed from specific adjacent compartments, depending on the particular application. The gradient optimization in fSLAM derives from tracking errors through the reconstruction process and includes those due to both inter- and intra-compartmental signal inhomogeneity. This differs from SLOOP's use of the SRF to minimize only the inter-compartmental leakage[5], while SLIM and GSLIM do not use optimized gradients.

Note also that the SRF is not global but is specific to the cardiac model. Inter- and intra-compartmental leakage occurs only when the integral over the entire compartment is non-zero or in the presence of significant heterogeneity. Compartmental segmentation in SLAM ensures that the integral of the SRF vanishes over other compartments, while fSLAM minimizes the effect of heterogeneity within the compartment of interest as well. Ultimately however, the spatial responses for SLAM and fSLAM and their compartmental contamination are fully characterized by determining the accuracy of the solutions and leakage errors, for which CSI is used as the standard in the current work (FIGS. 5, 7-10, Tables 1, 2).

Thus, the SLAM and fSLAM methods yield spectra comparable to the average of same-sized CSI compartments but with large scan-time reductions, SNR gains, and manageable, if not insignificant, bleed artifacts. The SNR gains predicted by Eq. (1) will be moderated in practice by the depth-dependence of the surface coil sensitivity, as well as the actual metabolite distribution (in our case, the myocardial wall thickness). Independent of the SNR gain, SLAM and fSLAM reduce the minimum scan-time required for localization from M acquisitions in CSI, to C or M'<<M. We believe that this efficiency advantage alone can dramatically reduce MRS scan-times for patient MRS studies employing CSI in global disease such as cardiomyopathies [15-20], large lesions, or where single voxel methods are limited by relaxation, motion or other considerations[21]. In addition, the significant reductions in minimum scan time provided by the SLAM and fSLAM methods compared to CSI, provides a practical pathway for translating the higher SNR afforded by increases in magnetic field strength, into faster MRS exams.

Embodiments of the current invention demonstrating extensions to higher than 1D are also included as follows. In one such example, SLAM is implemented with the steps: (i) Acquire MRI; (ii) Segment MRI into C compartments and overlay on the CSI grid; (iii) Apply M' central k-space phase encodes; and (iv) Reconstruct the spectra using SLAM. 2D- and 3D SLAM experiments were done in a 3T Philips MRI system on the human brain ($^1H$), and a phosphate phantom ($^{31}$P), respectively. The compartments were: scalp, brain, lateral ventricle and background (2D); and H$_3$PO$_4$, H$_3$PO$_2$ disk phantoms plus background (3D). An additional $^{31}$P heart study with chest, heart and background (1D) compartments is also shown. SLAM spectra were reconstructed with central 4 (1D), 7×7 (2D) and 2×4×2 (3D) phase-encodes, and compared with compartmental average CSI spectra obtained from the whole datasets with 16 (1D), 32×25 (2D), and 10×20×8 (3D) phase encodes. The heart study was ECG gated (TR=15.7 s); the brain study was lipid/water suppressed (TE/TR=0.144/3 s); and the phantom study had TR=0.72 s.

In 2D and 3D applications, subsets of the total number of phase encodes M' (<C) must be chosen for each of the two or three spatial dimensions. For example, in the 3D case, subsets of M'$_x$, M'$_y$, and M'$_z$ gradients must be chosen to apply phase-encoding in the x-, y-, and z-Cartesian directions respectively, as provided by the MRI/MRS scanner's spatially encoding gradient system. In this case, M'$_x$+M'$_y$, +M'$_z$=M'. For the 2D versions of SLAM or fSLAM, one of the M'$_x$, M'$_y$, or M'$_z$ is omitted depending on which dimensions are being encoded. The number of phase encodes used in any one direction, M'$_x$, M'$_y$, or M'$_z$, should at least not be less than the number of signal-generating compartments C$_x$, C$_y$, and C$_z$, that can be segmented in that dimension, ie, M'$_x$≥C$_x$, M'$_y$ ≥C$_y$, and M'$_z$≥C$_z$, etc. In general, the particular strategies for choosing the individual phase-encoding gradients in the subsets for each dimension, M'$_x$, M'$_y$, and M'$_z$, are as described above applied to each of the dimensions. For SNR optimization, the gradients are chosen from central k-space (for each dimension, k$_x$, k$_y$, and k$_z$), and can be integer multiples for SLAM, or fractional multiples for (SLAM, while not repeating the zero phase-encode (other than for the purpose of signal averaging). Similarly, gradient optimization for fSLAM can be treated as a separate application of the optimization algorithm for each M'$_x$, M'$_y$, and M'$_z$ in each dimension.

Figures 12A, 12B:
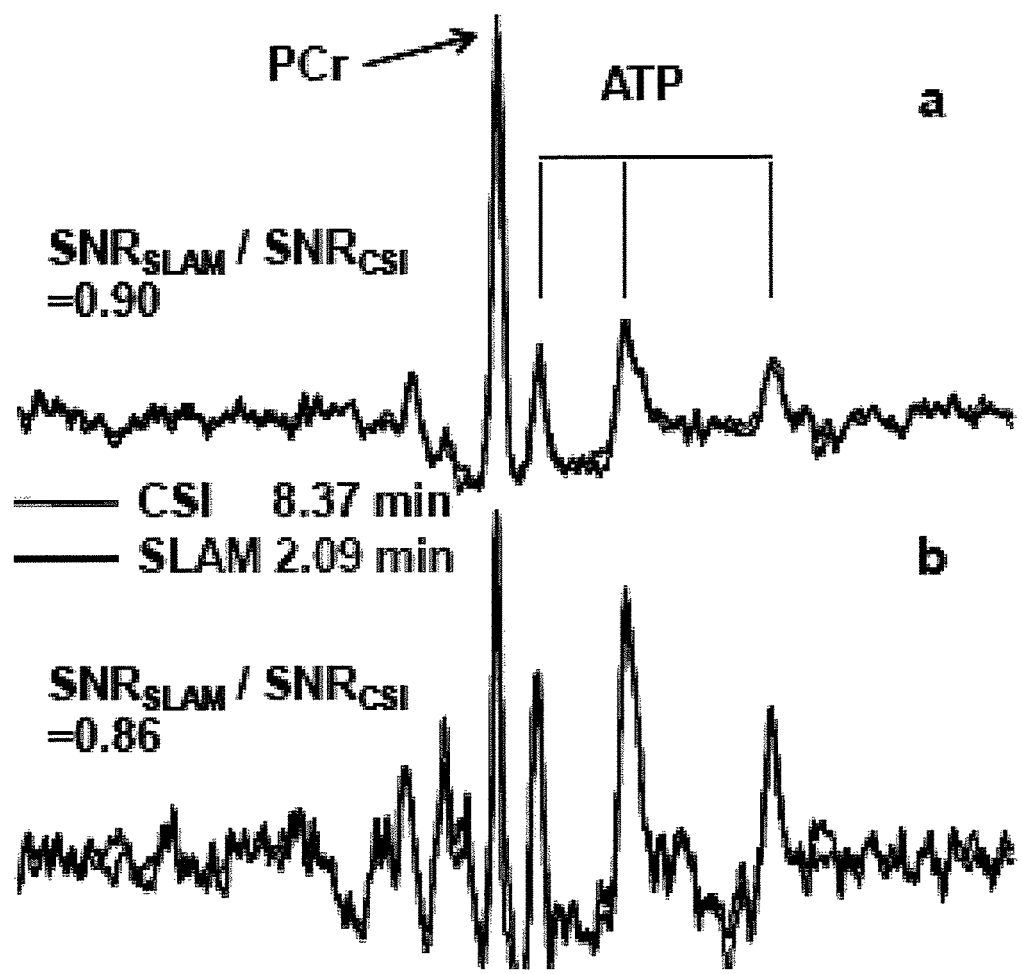
FIGS. 12A and 12B show an example of 1D cardiac $^{31}$P MRS (same volume, SLAM 4 times faster).
Figures 13A, 13B:
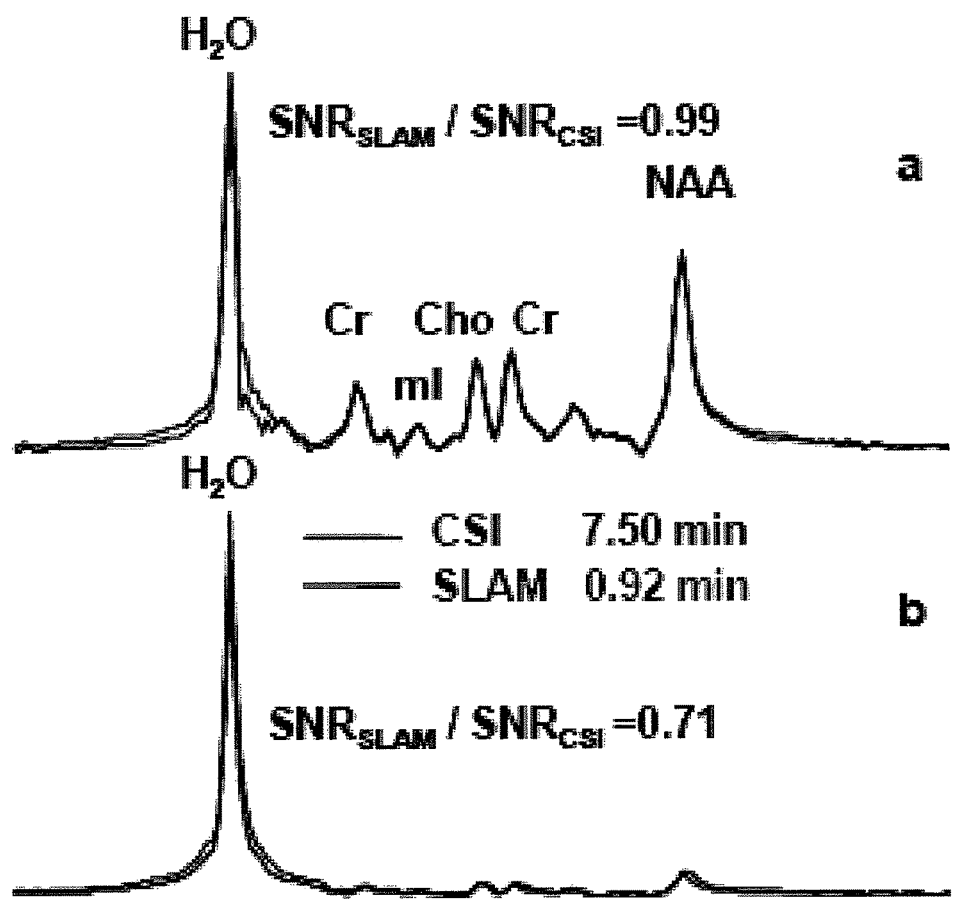
FIGS. 13A and 13B show an example of 2D brain $^1$H MRS (same volume, SLAM 16 times faster).

FIGS. 12A and 12B show $^{31}$P spectra for the same-sized chest (12A) and heart (12B) compartments reconstructed from 1D CSI and SLAM. FIGS. 13A and 13B show 2D SLAM and CSI spectra from the same brain (13A) and lateral ventricle (13B) volume. FIGS. 14A and 14B show H$_3$P$_{O2}$ (14A) and H$_{31}$P$_{O4}$ (14B) phantom spectra reconstructed from 3D CSI and SLAM. The speedup for the 1D, 2D and 3D SLAM compared with CSI are 4-, 16- and 100-fold, respectively: the SNR cost is 14%, <30% and 50%.

This new SLAM method applied in 1D, 2D and 3D yields spectra hardly distinguishable from the compartmental average spectra obtained from conventional CSI, while offering dramatic reductions in scan time not seen before.

REFERENCES

[1] P. A. Bottomley, C. J. Hardy, Strategies and Protocols for Clinical 31P Research in the Heart and Brain, Phil. Trans. R. Soc. Lond. A, 333 (1990) 531-544.

[2] T. R. Brown, B. M. Kincaid, K. Uguibil, NMR chemical shift imaging in three dimensions, Proc. Natl. Acad Sci USA, 79 (1982) 3523-3526.

[3] X. Hu, D. N. Levin, P. C. Lauterbur, T. Spraggins, SLIM: spectral localization by imaging, Magnetic Resonance in Medicine, 8 (1988) 314-322.

[4] Z. P. Liang, P. C. Lauterbur, A generalized series approach to MR spectrocopic imaging, IEEE Transactions Medical Imaging, 10 (1991) 132-137.

[5] M. von Kienlin, R. Mejia, Spectral localization with optimal pointspread function, Journal of Magnetic Resonance, 94 (1991) 268-287.

[6] Z. P. Liang, F. Boada, R. Constable, E. Haacke, P. Lauterbur, M. Smith, Constrained reconstruction methods in MR imaging, Rev Magn Reson Med, 4 (1992) 67-185.

[7] A. Bashir, D. A. Yablonskiy, Natural linewidth chemical shift imaging (NL☐CSI), Magnetic Resonance in Medicine, 56 (2006) 7-18.

[8] O. Khalidov, D. Van De VIIIe, M. Jacob, F. Lazeyras, M. Unser, BSLIM: Spectral Localization by Imaging With Explicit B0 Field Inhomogeneity Compensation, Medical Imaging, IEEE Transactions on, 26 (2007) 990-1000.

[9] M. Jacob, X. Zhu, A. Ebel, N. Schuff, Z. P. Liang, Improved model-based magnetic resonance spectroscopic imaging, Medical Imaging, IEEE Transactions on, 26 (2007) 1305-1318.

[10] L. An, S. Warach, J. Shen, Spectral localization by imaging using multielement receiver coils, Magnetic Resonance in Medicine, (2011).

[11] Z. Dong, J. H. Hwang, Lipid signal extraction by SLIM: Application to 1H MR spectroscopic imaging of human calf muscles, Magnetic Resonance in Medicine, 55 (2006) 1447-1453.

[12] J. A. Kmiecik, C. D. Gregory, Z. P. Liang, P. C. Lauterbur, M. J. Dawson, Lactate quantitation in a gerbil brain stroke model by GSLIM of multiple-quantum-filtered signals, J Magn Reson Imaging, 9 (1999) 539-543.

[13] R. Loffler, R. Sauter, H. Kolem, A. Haase, M. von Kienlin, Localized spectroscopy from anatomically matched compartments: improved sensitivity and localization for cardiac 31P MRS in humans, Journal of Magnetic Resonance, 134 (1998) 287-299.

[14] M. Meininger, W. Landschutz, M. Beer, T. Seyfarth, M. Horn, T. Pabst, A. Haase, D. Hahn, S, Neubauer, M. von Kienlin, Concentrations of human cardiac phosphorus metabolites determined by SLOOP $^{31}$P NMR spectroscopy, Magnetic Resonance in Medicine, 41 (1999) 657-663.

[15] M. von Kienlin, M. Beer, A. Greiser, D. Hahn, K. Harre, H. Kostler, W. Landschutz, T. Pabst, J. Sandstede, S, Neubauer, Advances in human cardiac 31P-MR spectroscopy: SLOOP and clinical applications, J Magn Reson Imaging, 13 (2001) 521-527.

[16] M. Beer, T. Seyfarth, J. Sandstede, W. Landschutz, C. Lipke, H. Kostler, M. von Kienlin, K. Harre, D. Hahn, S. Neubauer, Absolute concentrations of high-energy phosphate metabolites in normal, hypertrophied, and failing human myocardium measured noninvasively with 31P-SLOOP magnetic resonance spectroscopy, J Am Coll Cardiol, 40 (2002) 1267-1274.

[17] R. G. Weiss, P. A. Bottomley, C. J. Hardy, G. Gerstenblith, Regional Myocardial Metabolism of High-Energy Phosphates during Isometric Exercise in Patients with Coronary Artery Disease, N Engl J Med, 323 (1990) 1593-1600.

[18] M. A. Conway, P. A. Bottomley, R. Ouwerkerk, G. K. Radda, B. Rajagopalan, Mitral regurgitation: Impaired systolic function, eccentric hypertrophy, and increased severity are linked to lower phosphocreatine/ATP ratios in humans, Circulation, 97 (1998) 1716-1723.

[19] R. G. Weiss, G. Gerstenblith, P. A. Bottomley, ATP flux through creatine kinase in the normal, stressed, and failing human heart, Proc Natl Acad Sci USA, 102 (2005) 808-813.

[20] C. S. Smith, P. A. Bottomley, S. P. Schulman, G. Gerstenblith, R. G. Weiss, Altered Creatine Kinase Adenosine Triphosphate Kinetics in Failing Hypertrophied Human Myocardium, Circulation, 114 (2006) 1151-1158.

[21] P. A. Bottomley, NMR Spectroscopy of the Human Heart, in: R. K. Harris, R. E. Wasylishen (Eds.) Encyclopedia of Magnetic Resonance, John Wiley: Chichester, 2009.

[22] A.-M. El-Sharkawy, M. Schär, R. Ouwerkerk, R. G. Weiss, P. A. Bottomley, Quantitative cardiac 31P spectroscopy at 3 Tesla using adiabatic pulses, Magnetic Resonance in Medicine, 61 (2009) 785-795.

[23] R. A. Horn, C. R. Johnson, Matrix Analysis, Cambridge University Press, 1990.

[24] H. R. Brooker, T. H. Mareci, J. Mao, Selective Fourier transform localization, Magnetic Resonance in Medicine, 5 (1987) 417-433.

[25] R. E. Gabr, R. Ouwerkerk, P. A. Bottomely, Quantifying in vivo MR spectra with circles, Journal of Magnetic Resonance, 179 (2006) 152-163.

[26] P. A. Bottomley, Spatial localization in NMR spectroscopy in vivo, Annal NY Acad Sci, 508 (1987) 333-348.

[27] J. Frahm, H. Bruhn, M. L. Gyngell, K. D. Merboldt, W. Hanicke, R. Sauter, Localized high-resolution proton NMR spectroscopy using stimulated echoes: Initial applications to human brain in vivo, Magnetic Resonance in Medicine, 9 (1989) 79-93.

[28] R. Ordidge, A. Connelly, J. Lohman, Image-selected in vivo spectroscopy (ISIS). A new technique for spatially selective NMR spectroscopy, Journal of Magnetic Resonance (1969), 66 (1986) 283-294.

[29] L. P. Panych, L. Zhao, R. V. Mulkern, PSF□choice: A novel MRI method for shaping point□spread functions in phase□encoding dimensions, Magnetic Resonance in Medicine, 54 (2005) 159-168.

[30] P. A. Bottomley, C. J. Hardy, P. B. Roemer, R. G. Weiss, Problems and expediencies in human 31P spectroscopy. The definition of localized volumes, dealing with saturation and the technique-dependence of quantification, NMR in Biomedicine, 2 (1989) 284-289.

[31] Y. Zhang, R. E. Gabr, M. Schär, H. Zhu, P. Barker, R. G. Weiss, P. A. Bottomley, Dramatic speedup in 1D-, 2D- and 3D-MRS scan times with linear algebraic modeling (SLAM), in: Proceedings of the International Society for Magnetic Resonance in Medicine, in press, 2012.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of performing spatially localized magnetic resonance spectroscopy, comprising:
receiving a magnetic resonance image of an object;
identifying a plurality C of compartments that include all magnetic resonance spectroscopy signal sources in said object and at least one compartment of interest;
segmenting in at least one spatial dimension said magnetic resonance image of said object into said C compartments;
acquiring magnetic resonance spectroscopy signals from said compartments by applying a plurality M' of phase encodings applied in the at least one spatial dimension, wherein M'≥C, and wherein said plurality M' of phase encodings are further chosen from a central portion of a k-space representing said object to optimize at least one of a signal-to-noise ratio or a spatial selection of the at least one compartment of interest;
calculating a spatially localized magnetic resonance chemical shift spectrum from the at least one compartment of interest using a linear algebraic method; and
rendering a spatially localized magnetic resonance spectrum that is substantially equal to a spatial average of magnetic resonance chemical shift spectra from the at least one compartment of interest,
wherein said method provides an improved signal-to-noise ratio in at least one compartment of interest, as compared to a conventional chemical shift imaging process in which signals from all volume elements that contribute to the compartment are co-added, wherein said improvement is substantially proportionate to a square root of a ratio of a volume of the at least one compartment of interest to the volume resolution of said chemical shift imaging process.

2. A method of performing spatially localized magnetic resonance spectroscopy according to claim 1, wherein at least one of said plurality M' of phase encodings is a zero phase-encoding and at least one other of said plurality M' of phase encodings is an integer multiple of a smallest non-zero phase encoding.

3. A method of performing spatially localized magnetic resonance spectroscopy according to claim 1, wherein at least one of said plurality M' of phase encodings is a non-integer multiple of a smallest non-zero phase encoding.

4. A method of performing spatially localized magnetic resonance spectroscopy according to claim 3, wherein the choice of said plurality M' of phase encodings is further determined from said magnetic resonance image after segmentation,
wherein optimization of the signal-to-noise ratio in the at least one compartment of interest includes the selection of phase encodings from a central portion of the k-space representing said object, and
wherein optimization of the spatial selection of the at least one compartment of interest means minimization of at least one of the magnetic resonance spectroscopy signal arising from outside of said compartment of interest, or of erroneous signals arising from non-uniform magnetic resonance spectroscopy signal distributions arising within said compartment of interest.

5. A method of performing spatially localized magnetic resonance spectroscopy according to claim 4, wherein the choice of said plurality M' of phase encodings is based on a metric that optimizes both the signal-to-noise ratio and the spatial selection in the at least one compartment of interest.

6. A method of performing spatially localized magnetic resonance spectroscopy according to claim 1, wherein the at least one spatial dimension is one of two spatial dimensions or three spatial dimensions, and
wherein the M' of phase encodings are comprised of two or three subsets of phase encodings that are applied in the two or the three spatial dimensions, respectively.

7. A method of performing spatially localized magnetic resonance spectroscopy according to claim 6, wherein the number of phase encodings in each of said subset of phase encodings is greater than or equal to the number of compartments generating magnetic resonance spectroscopy signals that are segmented in the corresponding spatial dimensions of said object.

8. A method of performing spatially localized magnetic resonance spectroscopy according to claim 1, wherein the at least one compartment of interest is a plurality of compartments of interest.

9. A method of performing spatially localized magnetic resonance spectroscopy according to claim 1, said method providing spatially localized spectra from at least one compartment of interest in an acquisition time that is faster by a factor substantially equal to M/M' than the conventional chemical shift imaging process performed with M phase-encoding steps.

10. A magnetic resonance localized spectroscopy and imaging system, comprising:
a magnetic resonance imaging scanner; and
a data processing system configured to communicate with said magnetic resonance imaging scanner to receive magnetic resonance spectroscopy signals of an object,
wherein said data processing system is configured to:
receive a magnetic resonance image of said object,
display said magnetic resonance image to permit identification of a plurality C of compartments that include all magnetic resonance spectroscopy signal sources in said object and at least one compartment of interest,
segment in at least one spatial dimension said magnetic resonance image of said object into said C compartments,
receive magnetic resonance spectroscopy signals from said object corresponding to said magnetic resonance image by applying a plurality M' of phase encodings in at least one spatial dimension, wherein M'≥C, and wherein said plurality M' of phase encodings are further chosen from a central portion of a k-space representing said object to optimize at least one of a signal-to-noise ratio or a spatial selection of the at least one compartment of interest,
calculate a spatially localized magnetic resonance chemical shift spectrum from the at least one compartment of interest using a linear algebraic method, and
provide a spatially localized magnetic resonance spectrum substantially equal to a spatial average of the magnetic resonance chemical shift spectra from the at least one compartment of interest,
provide an improved signal-to-noise ratio in at least one compartment of interest, as compared to a conventional chemical shift imaging process in which signals from all volume elements that contribute to the compartment are co-added, wherein said improvement is substantially proportionate to a square root of a ratio of a volume of the at least one compartment of interest to the volume resolution of said chemical shift imaging process.

11. A magnetic resonance spectroscopy imaging and system according to claim 10, wherein at least one of said plurality M' of phase encodings is an integer multiple of a smallest non-zero phase encoding.

12. A magnetic resonance spectroscopy and imaging system according to claim 10, wherein at least one of said plurality M' of phase encodings is a non-integer multiple of a smallest non-zero phase encoding.

13. A magnetic resonance spectroscopy and imaging system according to claim 12, wherein a plurality of M' of phase encodings are provided which are determined from said magnetic resonance image after segmentation,
wherein said data processing system is further configured to perform at least one of:
optimization of the signal-to-noise ratio in the at least one compartment of interest which includes the selection of phase encodings from a central portion of the k-space of said object, and
optimization of the spatial selection of the at least one compartment of interest by minimization of at least one of the magnetic resonance spectroscopy signal arising from outside of said compartment of interest, or of erroneous signals arising from non-uniform magnetic resonance spectroscopy signal distributions arising within said compartment of interest.

14. A magnetic resonance spectroscopy and imaging system according to claim 13, wherein said plurality M' of phase encodings are provided by including a metric that optimizes both the signal-to-noise ratio and the spatial selection in the at least one compartment of interest.

15. A magnetic resonance spectroscopy and imaging system according to claim 10, wherein the at least one spatial dimension is one of two spatial dimensions or three spatial dimensions, and
wherein the plurality M' of phase encodings includes two or three subsets of phase encodings that are applied in the two or the three spatial dimensions, respectively.

16. A magnetic resonance spectroscopy and imaging system according to claim 15, wherein a number of phase encodings provided in each of said subset of phase encodings is greater than or equal to the number of compartments generating magnetic resonance spectroscopy signals that are segmented in the corresponding spatial dimensions of said object.

17. A magnetic resonance spectroscopy and imaging system according to claim 10, wherein the at least one compartment of interest is a plurality of compartments of interest.

* * * * *